(12) United States Patent
Defossa et al.

(10) Patent No.: US 6,506,778 B2
(45) Date of Patent: Jan. 14, 2003

(54) ACYLPHENYLUREA DERIVATIVES, A PROCESS FOR THEIR PREPARATION AND THEIR USE AS PHARMACEUTICALS

(75) Inventors: Elisabeth Defossa, Idstein (DE); Thomas Klabunde, Frankfurt (DE); Hans-Joerg Burger, Hofheim (DE); Andreas Herling, Bad Camberg (DE); Karl-Heinz Baringhaus, Wölfersheim (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/875,901

(22) Filed: Jun. 8, 2001

(65) Prior Publication Data

US 2002/0151586 A1 Oct. 17, 2002

(30) Foreign Application Priority Data

Jun. 9, 2000 (DE) .......................... 100 28 175
Apr. 4, 2001 (DE) .......................... 101 16 768

(51) Int. Cl.$^7$ ..................... A61K 31/445; C07D 211/08
(52) U.S. Cl. .................. 514/331; 546/237; 546/247; 549/496; 560/19; 562/512; 562/579; 564/44; 514/461; 514/532; 514/571; 514/594
(58) Field of Search ................ 514/331, 461, 514/532, 571, 594; 546/247, 237; 549/496; 560/19; 562/512, 579; 564/44

(56) References Cited

U.S. PATENT DOCUMENTS 3,718,660 A 2/1973 Plumpe et al.

FOREIGN PATENT DOCUMENTS

EP 0 632 019 A1 1/1995

OTHER PUBLICATIONS

Wie, S.I. et al.: Comparison of coating and immunizing antigen structure on the sensitivity and specificity of immunoassays for benzoylphenylurea insecticides. J. Agric. food sci. vol. 32, pp. 1294–1301, 1984.*

* cited by examiner

Primary Examiner—Charanjit S. Aulakh
(74) Attorney, Agent, or Firm—Finnegan, Henderson, Farabow, Garrett & Dunner, LLP

(57) ABSTRACT

The invention is directed to acylphenylurea derivatives and their physiologically tolerated salts and physiologically functional derivatives.

Compounds of the formula I

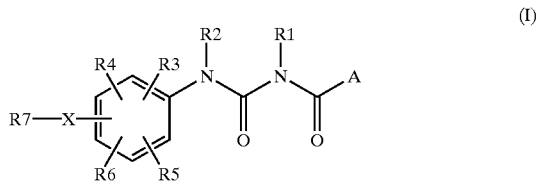

in which the radicals have the stated meanings, and their physiologically tolerated salts and a process for their preparation are described. The compounds are suitable, for example, for treating type II diabetes.

18 Claims, No Drawings

ACYLPHENYLUREA DERIVATIVES, A PROCESS FOR THEIR PREPARATION AND THEIR USE AS PHARMACEUTICALS

This application claims priority benefit of Federal Republic of Germany Application 10028175.3-42, filed Jun. 9, 2000, and Federal Republic of Germany Application 10116768.7 filed Apr. 4, 2001, both of which are incorporated by reference.

The invention is directed to acylphenylurea derivatives, their physiologically tolerated salts, and their physiologically functional derivatives.

Acylphenylurea derivatives have already been described as insecticides (EP 0 136 745, EP 0 167 197, DE 29 26 480, J. Agric. Food Chem. 1999, 47, 3116–3424, which are incorporated by reference).

In one embodiment, the invention provides compounds that display a blood glucose-lowering effect, which can be exploited therapeutically.

These include compounds of the formula (I)

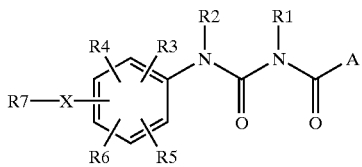

(I)

in which

A is phenyl, naphthyl, it being possible for the phenyl or naphthyl radical to be substituted up to three times by: F, Cl, Br, OH, $CF_3$, $NO_2$, CN, $OCF_3$, O—$(C_1-C_6)$-alkyl, O—$(C_1-C_6)$-alkenyl, O—$(C_1-C_6)$-alkynyl, S—$(C_1-C_6)$-alkyl, S—$(C_1-C_6)$-alkenyl, S—$(C_1-C_6)$-alkynyl, SO—$(C_1-C_6)$-alkyl, $SO_2$—$(C_1-C_6)$-alkyl, $SO_2$—$NH_2$, $(C_1-C_6)$-alkyl, $(C_1-C_6)$-alkenyl, $(C_1-C_6)$-alkynyl, $(C_3-C_7)$-cycloalkyl, $(C_3-C_7)$-cycloalkyl-$(C_1-C_4)$-alkylene, $(C_0-C_6)$-alkylene-COOH, $(C_0-C_6)$-alkylene-COO$(C_1-C_7)$-alkyl, $CONH_2$, CONH $(C_1-C_6)$-alkyl, CON[$(C_1-C_6)$-alkyl)]$_2$, CONH $(C_3-C_6)$-cycloalkyl, $(C_0-C_6)$-alkylene-$NH_2$, $(C_0-C_6)$-alkylene-NH($C_2-C_6$)-alkyl, $(C_0-C_6)$-alkylene-N[$(C_1-C_6)$-alkyl]$_2$, NH—CO—$(C_1-C_6)$-Alkyl, NH—CO-phenyl, or NH—$SO_2$-phenyl, it being possible for the phenyl ring to be substituted up to twice by F, Cl, CN, OH, $(C_1-C_6)$-alkyl, O—$(C_1-C_6)$-alkyl, $CF_3$, $OCF_3$, COOH, COO($C_1-C_6$)-alkyl or $CONH_2$;

R1, R2 are, independently of one another, H, $(C_1-C_6)$-alkyl, O—$(C_1-C_6)$-alkyl, CO—$(C_1-C_6)$-alkyl, COO—$(C_1-C_6)$-alkyl, $(C_1-C_6)$-alkylene-COOH, or $(C_1-C_6)$-alkylene-COO—$(C_1-C_6)$-alkyl;

R3, R4, R5, R6 are, independently of one another, H, F, Cl, Br, OH, $CF_3$, $NO_2$, CN, $OCF_3$, O—$(C_1-C_6)$-alkyl, O—$(C_1-C_6)$-alkenyl, O—$(C_1-C_6)$-alkynyl, S—$(C_1-C_6)$-alkyl, S—$(C_1-C_6)$-alkenyl, S—$(C_1-C_6)$-alkynyl, SO—$(C_1-C_6)$-alkyl, $SO_2$—$(C_1-C_6)$-alkyl, $SO_2$—$NH_2$, $(C_1-C_6)$-alkyl, $(C_1-C_6)$-alkenyl, $(C_1-C_6)$-alkynyl, $(C_3-C_7)$-cycloalkyl, $(C_3-C_7)$-cycloalkyl-$(C_1-C_4)$-alkylene, COOH, COO[$(C_1-C_6)$-alkyl], $CONH_2$, CONH($C_1-C_6$)-alkyl, CON[$(C_1-C_6)$-alkyl]$_2$, CONH($C_3-C_7$)-cycloalkyl, $NH_2$, NH($C_1-C_6$)-alkyl, N[$(C_1-C_6)$-alkyl]$_2$, NH—CO—$(C_1-C_6)$-alkyl, NH—CO-phenyl, or NH—$SO_2$-phenyl, it being possible for the phenyl ring to be substituted up to twice by F, Cl, CN, OH, $(C_1-C_6)$-Alkyl, O—$(C_1-C_6)$-alkyl, $CF_3$, $OCF_3$, COOH, COO($C_1-C_6$)-alkyl or $CONH_2$;

X is O or S;

R7 is $(C_1-C_{10})$-alkylene-COOH, $(C_6-C_{10})$-alkylene-COO—$(C_1-C_6)$-alkyl, $(C_1-C_{10})$-alkylene-$CONH_2$, $(C_1-C_{10})$-alkylene-CONH—$(C_1-C_6)$-alkyl, $(C_1-C_{10})$-alkylene-CON—[$(C_1-C_6)$-alkyl]$_2$, $(C_1-C_{10})$-alkylene-$NH_2$, $(C_1-C_{10})$-alkylene-NH($C_1-C_6$)-alkyl, $(C_1-C_{10})$-alkylene-N[$(C_1-C_6)$-alkyl]$_2$, or $(C_1-C_{10})$-alkylene-B;

B is $(C_3-C_7)$-cycloalkyl, phenyl, pyrrolyl, Imidazolyl, thiazolyl, azetidinyl, thienyl, piperidinyl, pyrrolidinyl, morpholinyl, pyridyl-methyl or furyl, in which cycloalkyl, phenyl, pyrrolyl, imidazolyl, thiazolyl, azetidinyl, thienylmethyl, piperidinyl, pyrrolidinyl, morpholinyl, pyridyl or furyl may in each case be substituted up to twice by Cl, F, CN, $CF_3$, $OCF_3$, COOH, COO—$(C_1-C_6)$-alkyl, $CONH_2$, CONH—$(C_1-C_6)$-alkyl, CON—[$(C_1-C_6)$-alkyl]$_2$, $(C_1-C_6)$-alkyl, OH, or O—$(C_1-C_6)$-alkyl;

and their physiologically tolerated salts thereof, except the compounds of the formula:

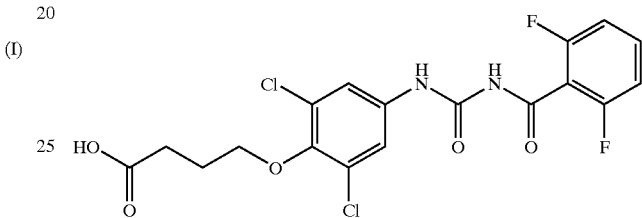

and compounds of the formula (I) in which the radicals are, at the same time:

| A | phenyl; |
|---|---|
| X | O; |
| R1 | H; |
| R7 | -$(C_1-C_4)$-alkyl-B; |
| B | $(C_3-C_7)$-cycloalkyl, or a heteroaryl. |

Compounds of the formula (I) can include those in which

A is phenyl, naphthyl, it being possible for the phenyl or naphthyl radical to be substituted up to three times by F, Cl, Br, OH, $CF_3$, $NO_2$, CN, $OCF_3$, O—$(C_1-C_6)$-alkyl, O—$(C_1-C_6)$-alkenyl, O—$(C_1-C_6)$-alkynyl, S—$(C_1-C_6)$-alkyl, S—$(C_1-C_6)$-alkenyl, S—$(C_1-C_6)$-alkynyl, SO—$(C_1-C_6)$-alkyl, $SO_2$—$(C_1-C_6)$-alkyl, $SO_2$—$NH_2$, $(C_1-C_6)$-alkyl, $(C_1-C_6)$-alkenyl, $(C_1-C_6)$-alkynyl, $(C_3-C_7)$-cycloalkyl, $(C_3-C_7)$-cycloalkyl-$(C_1-C_4)$-alkylene, $(C_0-C_6)$-alkylene-COOH, $(C_0-C_6)$-alkylene-COO($C_1-C_6$)-alkyl, $CONH_2$, CONH $(C_1-C_6)$-alkyl, CON[$(C_1-C_6)$-alkyl]$_2$, CONH($C_3-C_7$)-cycloalkyl, $(C_0-C_6)$-alkylene-$NH_2$, $(C_0-C_6)$-alkylene-NH($C_2-C_6$)-alkyl, $(C_0-C_6)$-alkylene-N[$(C_1-C_6)$-alkyl]$_2$, NH—CO—$(C_1-C_6)$-alkyl, NH—CO-phenyl, or NH—$SO_2$-phenyl, it being possible for the phenyl ring to be substituted up to twice by F, Cl, CN, OH, $(C_1-C_6)$-alkyl, O—$(C_1-C_6)$-alkyl, $CF_3$, $OCF_3$, COOH, COO($C_1-C_6$)-alkyl or $CONH_2$;

R1, R2 are, independently of one another, H, $(C_1-C_6)$-alkyl, O—$(C_1-C_6)$-alkyl, CO—$(C_1-C_6)$-alkyl, COO—$(C_1-C_6)$-alkyl, $(C_1-C_6)$-alkylene-COOH, or $C_1-C_6$-alkylene-COO—$(C_1-C_6)$-alkyl;

R3, R4, R5, R6 are, independently of one another, H, F, Cl, Br, OH, $CF_3$, $NO_2$, CN, $OCF_3$, O—$(C_1-C_6)$-alkyl, O—$(C_1-C_6)$-alkenyl, O—$(C_1-C_6)$-alkynyl, S—$(C_1-C_6)$-alkyl, S—$(C_1-C_6)$-alkenyl, S—$(C_1-C_6)$- alkynyl, SO—($C_1$–$C_6$)-alkyl, $SO_2$—($C_1$–$C_6$)-alkyl, $SO_2$—$NH_2$, ($C_1$–$C_6$)-alkyl, ($C_1$–$C_6$)-alkenyl, ($C_1$–$C_6$)-alkynyl, ($C_3$–$C_7$)-cycloalkyl, ($C_3$–$C_7$)-cycloalkyl-($C_1$–$C_4$)-alkylene, COOH, COO($C_1$–$C_6$)-alkyl, $CONH_2$, CONH($C_1$–$C_6$)-alkyl, CON[($C_1$–$C_6$)-alkyl]$_2$, CONH($C_3$–$C_7$)-cycloalkyl, $NH_2$, NH($C_1$–$C_6$)-alkyl, N[($C_1$–$C_6$)-alkyl]$_2$, NH—CO—($C_1$–$C_6$)-alkyl, or NH—CO-phenyl, NH—$SO_2$-phenyl, it being possible for the phenyl ring to be substituted up to twice by F, Cl, CN, OH, ($C_1$–$C_6$)-alkyl, O—($C_1$–$C_6$)-alkyl, $CF_3$, $OCF_3$, COOH, COO($C_1$–$C_6$)-alkyl or $CONH_2$;

X is O or S;

R7 is ($C_1$–$C_{10}$)-alkylene-COOH, ($C_6$–$C_{10}$)-alkylene-COO—($C_1$–$C_6$)-alkyl, ($C_1$–$C_{10}$)-alkylene-$CONH_2$, ($C_1$–$C_{10}$)-alkylene-CONH—($C_1$–$C_6$)-alkyl, ($C_1$–$C_{10}$)-alkylene-CON—[($C_1$–$C_6$)-alkyl]$_2$, ($C_1$–$C_{10}$)-alkylene-$NH_2$, ($C_1$–$C_{10}$)-alkylene-NH($C_1$–$C_6$)-alkyl, ($C_1$–$C_{10}$)-alkylene-N[($C_1$–$C_6$)-alkyl]$_2$, or ($C_1$–$C_{10}$)-alkylene-B;

B is ($C_3$–$C_7$)-cycloalkyl, phenyl, pyrrolyl, imidazolyl, thiazolyl, azetidinyl, thienylmethyl, piperidinyl, pyrrolidinyl, morpholinyl, pyridyl-methyl or furyl, in which cycloalkyl, phenyl, pyrrolyl, imidazolyl, thiazolyl, azetidinyl, thienyl, piperidinyl, pyrrolidinyl, morpholinyl, pyridyl or furyl may in each case be substituted up to twice by Cl, F, CN, $CF_3$, $OCF_3$, COOH, COO—($C_1$–$C_6$)-alkyl, $CONH_2$, CONH—($C_1$–$C_6$)-alkyl, CON—[($C_1$–$C_6$)-alkyl]$_2$, ($C_1$–$C_6$)-alkyl, OH, or O—($C_1$–$C_6$)-alkyl and their physiologically tolerated salts thereof,
except the compounds of the formula

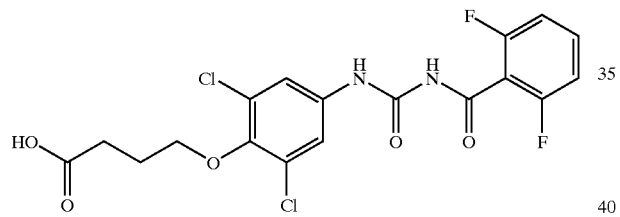

and compounds of the formula (I) in which the radicals are, at the same time:

| A | phenyl; |
|---|---|
| X | O; |
| R1 | H; |
| R7 | -($C_1$–$C_4$)-alkyl-B; |
| B | ($C_3$–$C_7$)-cycloalkyl, or heteroaryl. |

Further examples of compounds of the formula (I) are those in which

A is phenyl, it being possible for the phenyl radical to be substituted up to twice by F, Cl, Br, or O—($C_1$–$C_6$)-alkyl;

R1, R2 are, independently of one another, H, ($C_1$–$C_6$)-alkyl, or CO—($C_1$–$C_6$)-alkyl;

R3, R4, R5, R6 are, independently of one another, H, Cl, F, ($C_1$–$C_6$)-alkyl, O—($C_1$–$C_6$)-alkyl, or —COO—($C_1$–$C_6$)-alkyl;

X is O;

R7 is ($C_1$–$C_{10}$)-alkylene-COOH, ($C_6$–$C_{10}$)-alkylene-COO—($C_1$–$C_6$)-alkyl, or ($C_1$–$C_{10}$)-alkylene-$CONH_2$;

and their physiologically tolerated salts thereof, except the compounds of the formula:

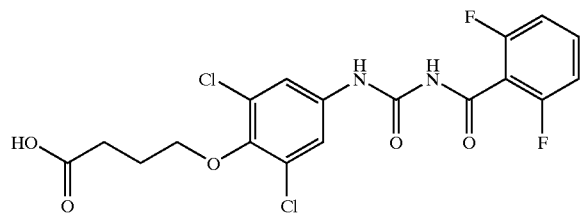

In another embodiment, the invention relates to the use of compounds of the formula (I)

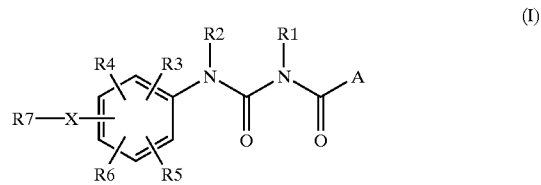

in which

A is phenyl, naphthyl, it being possible for the phenyl or naphthyl radical to be substituted up to three times by F, Cl, Br, OH, $CF_3$, $NO_2$, CN, $OCF_3$, O—($C_1$–$C_6$)-alkyl, O—($C_1$–$C_6$)-alkenyl, O—($C_1$–$C_6$)-alkynyl, S—($C_1$–$C_6$)-alkyl, S—($C_1$–$C_6$)-alkenyl, S—($C_1$–$C_6$)-alkynyl, SO—($C_1$–$C_6$)-alkyl, $SO_2$—($C_1$–$C_6$)-alkyl, $SO_2$—$NH_2$, ($C_1$–$C_6$)-alkyl, ($C_1$–$C_6$)-alkenyl, ($C_1$–$C_6$)-alkynyl, ($C_3$–$C_7$)-cycloalkyl, ($C_3$–$C_7$)-cycloalkyl-($C_1$–$C_4$)-alkylene, ($C_0$–$C_6$)-alkylene-COOH, ($C_0$–$C_6$)-alkylene-COO($C_1$–$C_6$)-alkyl, $CONH_2$, CONH($C_1$–$C_6$)-alkyl, CON[($C_1$–$C_6$)-alkyl]$_2$, CONH($C_3$–$C_7$)-cycloalkyl, ($C_0$–$C_6$)-alkylene-$NH_2$, ($C_0$–$C_6$)-alkylene-NH($C_1$–$C_6$)-alkyl, ($C_0$–$C_6$)-alkylene-N[($C_1$–$C_6$)-alkyl]$_2$, NH—CO—($C_1$–$C_6$)-alkyl, NH—CO-phenyl, or NH—$SO_2$-phenyl, it being possible for the phenyl ring to be substituted up to twice by F, Cl, CN, OH, ($C_1$–$C_6$)-alkyl, O—($C_1$–$C_6$)-alkyl, $CF_3$, $OCF_3$, COOH, COO($C_1$–$C_6$)-alkyl or $CONH_2$;

R1, R2 are, independently of one another, H, ($C_1$–$C_6$)-alkyl, O—($C_1$–$C_6$)-alkyl, CO—($C_1$–$C_6$)-alkyl, COO—($C_1$–$C_6$)-alkyl, ($C_1$–$C_6$)-alkylene-COOH, or ($C_1$–$C_6$)-alkylene-COO—($C_1$–$C_6$)-alkyl;

R3, R4, R5, R6 are, independently of one another, H, F, Cl, Br, OH, $CF_3$, $NO_2$, CN, $OCF_3$, O—($C_1$–$C_6$)-alkyl, O—($C_1$–$C_6$)-alkenyl, O—($C_1$–$C_6$)-alkynyl, S—($C_1$–$C_6$)-alkyl, S—($C_1$–$C_6$)-alkenyl, S—($C_1$–$C_6$)-alkynyl, SO—($C_1$–$C_6$)-alkyl, $SO_2$—($C_1$–$C_6$)-alkyl, $SO_2$—$NH_2$, ($C_1$–$C_6$)-alkyl, ($C_1$–$C_6$)-alkenyl, ($C_1$–$C_6$)-alkynyl, ($C_3$–$C_7$)-cycloalkyl, ($C_3$–$C_7$)-cycloalkyl-($C_1$–$C_4$)-alkylene, COOH, COO($C_1$–$C_6$)-alkyl, $CONH_2$, CONH($C_1$–$C_6$)-alkyl, CON[($C_1$–$C_6$)-alkyl]$_2$, CONH($C_3$–$C_7$)-cycloalkyl, $NH_2$, NH($C_1$–$C_6$)-alkyl, N[($C_1$–$C_6$)-alkyl]$_2$, NH—CO—($C_1$–$C_6$)-alkyl, NH—CO-phenyl, or NH—$SO_2$-phenyl, it being possible for the phenyl ring to be substituted up to twice by F, Cl, CN, OH, ($C_1$–$C_6$)-Alkyl, O—($C_1$–$C_6$)-alkyl, $CF_3$, $OCF_3$, COOH, COO($C_1$–$C_6$)-alkyl or $CONH_2$;

X is O or S;

R7 is ($C_1$–$C_{10}$)-alkylene-COOH, ($C_1$–$C_{10}$)-alkylene-COO—($C_1$–$C_6$)-alkyl, ($C_1$–$C_{10}$)-alkylene-$CONH_2$, ($C_1$–$C_{10}$)-alkylene-CONH—($C_1$–$C_6$)-alkyl, ($C_1$–$C_{10}$)-alkylene-CON—[($C_1$–$C_6$)-alkyl]$_2$, ($C_1$–$C_{10}$)-alkylene-$NH_2$, ($C_1$–$C_{10}$)-alkylene-NH($C_1$–$C_6$)-alkyl, ($C_1$–$C_{10}$)-alkylene-N[($C_1$–$C_6$)-alkyl]$_2$, or ($C_1$–$C_{10}$)-alkylene-B;

B is $(C_3–C_7)$-cycloalkyl, phenyl, pyrrolyl, Imidazolyl, thiazolyl, azetidinyl, thienyl, piperidinyl, pyrrolidinyl, morpholinyl, pyridyl or furyl, in which cycloalkyl, phenyl, pyrrolyl, imidazolyl, thiazolyl, azetidinyl, thienyl, piperidinyl, pyrrolidinyl, morpholinyl, pyridyl or furyl may in each case be substituted up to twice by Cl, F, CN, $CF_3$, $OCF_3$, COOH, COO—$(C_1–C_6)$-alkyl, $CONH_2$, CONH—$(C_1–C_6)$-alkyl, CON—$[(C_1–C_6)$-alkyl$]_2$, $(C_1–C_6)$-alkyl, OH, or O—$(C_1–C_6)$-alkyl;

and their physiologically tolerated salts thereof, for producing a medicine for lowering the blood glucose level and treating type II diabetes.

In another embodiment, the invention relates to compounds of the formula (I) in the form of their racemates, racemic mixtures and pure enantiomers, and to their diastereomers and mixtures thereof.

The alkyl radicals in the substituents R1, R2, R3, R4, R5, R6, R7, A and B may be both straight-chain and branched.

Pharmaceutically acceptable salts are particularly suitable for medical applications because of their greater solubility in water compared with the initial or basic compounds. These salts must have a pharmaceutically acceptable anion or cation. Suitable pharmaceutically acceptable acid addition salts of the compounds of the invention are salts of inorganic acids such as, for example, hydrochloric acid, hydrobromic, phosphoric, metaphosphoric, nitric, sulfamic and sulfuric acids, and organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acids. Suitable pharmaceutically acceptable basic salts are ammonium salts, alkali metal salts (such as sodium and potassium salts) and alkaline earth metal salts (such as magnesium and calcium salts).

Salts with pharmaceutically unacceptable anions such as, for example, trifluoroacetate, likewise belong within the framework of the invention as useful intermediates for the preparation or purification of pharmaceutically acceptable salts and/or use in nontherapeutic, for example in vitro, applications.

The term "physiologically functional derivative" used herein refers to any physiologically tolerated derivative of a compound of the formula (I) of the invention, for example an ester, which on administration to a mammal such as, for example, a human is able to form (directly or indirectly) a compound of the formula (I) or an active metabolite thereof.

Physiologically functional derivatives include prodrugs of the compounds of the invention, as described, for example, in H. Okada et al., Chem. Pharm. Bull. 1994, 42, 57–61, the relevant disclosure of which is herein incorporated by reference. Such prodrugs can be metabolized in vivo producing a compound of the invention. These prodrugs may themselves be active or not.

The compounds of the invention may also exist in various polymorphous forms, for example as amorphous and crystalline polymorphous forms. All polymorphous forms of the compounds of the invention belong within the framework of the invention and are a further aspect of the invention.

All references to "compound(s) of formula (I)" hereinafter refer to compound(s) of the formula (I) as described above, and their salts, solvates and physiologically functional derivatives as described herein.

The amount of a compound of formula (I) that can achieve the desired biological effect depends on a number of factors, for example the specific compound chosen, the intended use, the mode of administration and the clinical condition of the patient. The daily dose is generally in the range from about 0.3 mg to about 100 mg (typically from about 3 mg to about 50 mg) per day and per kilogram of bodyweight, for example about 3–10 mg/kg/day. An intravenous dose may be, for example, in the range from about 0.3 mg to about 1.0 mg/kg, which can suitably be administered as infusion of about 10 ng to about 100 ng per kilogram and per minute. Suitable infusion solutions for these purposes may contain, for example, from about 0.1 ng to about 10 mg, typically from about 1 ng to about 10 mg, per milliliter. Single doses may contain, for example, from about 1 mg to about 10 g of the active ingredient. Thus, ampoules for injections may contain, for example, from about 1 mg to about 100 mg, and single-dose formulations, which can be administered orally, such as, for example, capsules or tablets, may contain, for example, from about 1.0 to about 1000 mg, typically from about 10 to about 600 mg. For the therapy of the above-mentioned conditions, the compounds of formula (I) may be used as the compound itself, but they are typically in the form of a pharmaceutical composition with an acceptable carrier. The carrier must, of course, be acceptable in the sense that it is compatible with the other ingredients of the composition and is not harmful to the patient's health. The carrier may be a solid or a liquid or both, and is typically formulated with the compound as a single dose, for example as a tablet, which may contain from about 0.05% to about 95% by weight of the active ingredient. Other pharmaceutically active substances may likewise be present in the pharmaceutical composition, including other compounds of formula (I). The pharmaceutical compositions of the invention can be produced by one of the known pharmaceutical methods, which essentially consist of mixing the ingredients with pharmacologically acceptable carriers and/or excipients.

Pharmaceutical compositions of the invention are those suitable for oral, rectal, topical, peroral (for example sublingual) and parenteral (for example subcutaneous, intramuscular, intradermal or intravenous) administration, although the most suitable mode of administration depends in each individual case, on the nature and severity of the condition to be treated, and on the nature of the compound of formula (I) used in each case. Coated formulations and coated slow-release formulations also belong within the framework of the invention, as well as acid- and gastric juice-resistant formulations. Suitable coatings resistant to gastric juice comprise cellular acetate, phthalate, polyvinyl acetate phthalate, hydroxypropylmethylcellulose phthalate and anionic polymers of methacrylic acid and methyl methacrylate.

Suitable pharmaceutical compounds for oral administration may be in the form of several units such as, for example, capsules, wafers, suckable tablets or tablets, each of which contains a defined amount of the compound of formula (I); as powders or granules, as solution or suspension in an aqueous or nonaqueous liquid; or as an oil-in-water or water-in-oil emulsion. These compositions may, as already mentioned, be prepared by any suitable pharmaceutical method that includes a step in which the active ingredient and the carrier, (which may consist of one or more additional ingredients) are brought into contact. The compositions are generally produced by uniform and homogeneous mixing of the active ingredient with a liquid and/or finely divided solid carrier, after which the product is shaped if necessary. Thus, for example, a tablet can be produced by compressing or molding a powder or granules of the compound, with one or more additional ingredients when appropriate. Compressed tablets can be produced by tableting the compound in free-flowing form such as, for example, a powder or granules, where appropriate mixed with a binder, glidant, inert diluent and/or one or more surface-active/dispersing agent(s) in a suitable machine. Molded tablets can be produced by molding the compound, in powder form and moistened, with an inert liquid diluent in a suitable machine.

Pharmaceutical compositions which are suitable for peroral (sublingual) administration comprise suckable tablets, which contain a compound of formula (I) with a flavoring, normally sucrose and gum arabic or tragacanth, and pastilles, which comprise the compound in an inert base such as gelatin and glycerol or sucrose and gum arabic.

The pharmaceutical compositions suitable for parenteral administration comprise aqueous preparations of a compound of formula (I), these preparations can be sterile and/or isotonic with the blood of the intended recipient. These preparations can be administered intravenously, although administration may also take place by subcutaneous, intramuscular or intradermal injection. These preparations can be produced by mixing the compound with water and making the resulting solution sterile and isotonic with blood. Injectable compositions of the invention generally contain from about 0.1 to about 5% by weight of the active compound.

Pharmaceutical compositions suitable for rectal administration are typically in the form of single-dose suppositories. These can be produced by mixing a compound of the formula (I) with one or more conventional solid carriers, for example cocoa butter, and shaping the resulting mixture.

Pharmaceutical compositions suitable for topical use on the skin are typically in the form of ointment, crème, lotion, paste, spray, aerosol or oil. Carriers that can be used include petrolatum, lanolin, polyethylene glycols, alcohols and combinations of two or more of these substances. The active ingredient is generally present in a concentration from about 0.1 to about 15% by weight of the composition, for example from about 0.5 to about 2%.

Transdermal administration is also possible. Pharmaceutical compositions suitable for transdermal uses can be in the form of single plasters, which are suitable for long-term close contact with the patient's epidermis. Such plasters suitably contain the active ingredient in an aqueous solution, which is buffered where appropriate, dissolved and/or dispersed in an adhesive or dispersed in a polymer. A suitable active ingredient concentration is about 1% to about 35%, typically about 3% to about 15%. Another possibility is for the active ingredient to be released by electrotransport or iontophoresis as described, for example, in Pharmaceutical Research, 2(6): 318 (1986), which is herein incorporated by reference.

The invention is further directed to a process for preparing the compounds of the formula (I), which comprises obtaining the compounds of the formula (I) by proceeding as shown in the following reaction:

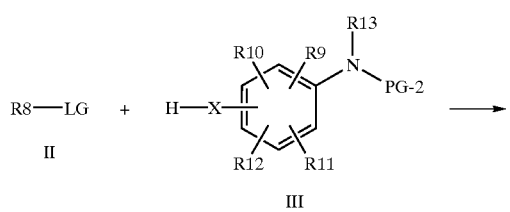

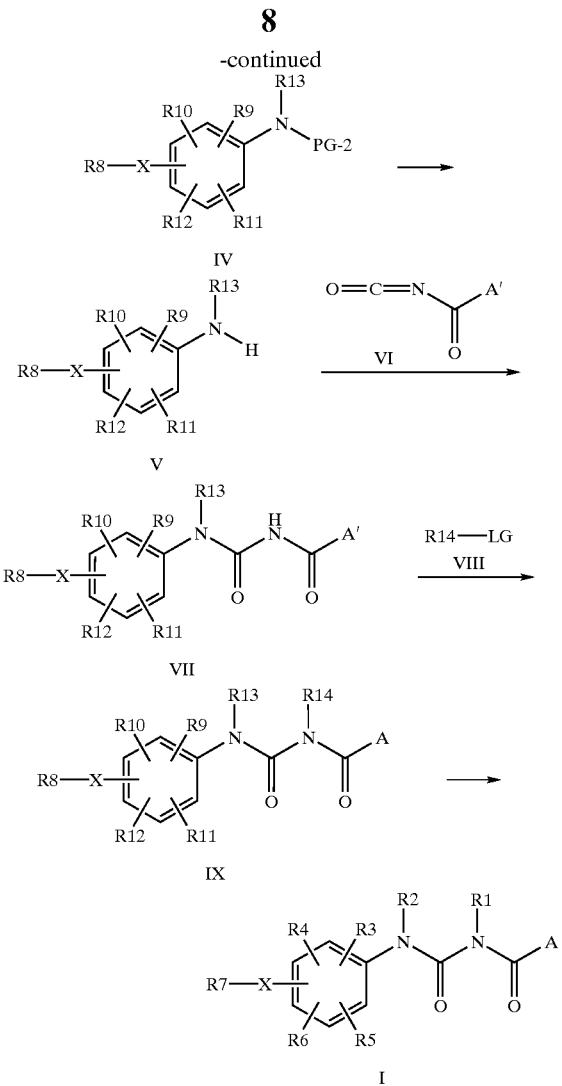

Compounds of the formula (II) include:

$$R8\text{—}LG \qquad (II)$$

in which

R8 is $(C_1-C_{10})$-alkylene-COO—(PG-1), $(C_6-C_{10})$-alkylene-COO—$(C_1-C_6)$-alkyl, $(C_1-C_{10})$-alkylene-CON—$(PG\text{-}2)_2$, $(C_1-C_{10})$-alkylene-CONH—$(C_1-C_6)$-alkyl, $(C_1-C_{10})$-alkylene-CON—$[(C_1-C_6)\text{-alkyl}]_2$, $(C_1-C_{10})$-alkylene-N—$(PG\text{-}2)_2$, $(C_1-C_{10})$-alkylene-NH$(C_1-C_6)$-alkyl, $(C_1-C_{10})$-alkylene-N$[(C_1-C_6)\text{-alkyl}]_2$, or $(C_1-C_{10})$-alkylene-B', wherein PG-1 is a generally known protective group for esters, such as, for example, $(C_1-C_6)$-alkyl, benzyl or p-methoxybenzyl, and PG-2 is a generally known protective group for amino groups, such as, for example, $(C_1-C_6)$-alkylcarbonyl, $(C_1-C_6)$-alkyloxycarbonyl or $(C_6-C_{12})$-aryl-$(C_1-C_4)$-alkyloxycarbonyl, PG-2 replaces either both hydrogens or only one hydrogen atom in the amino group, and B' is $(C_3-C_7)$-cycloalkyl, $(C_3-C_7)$-cycloalkyl-$(C_1-C_4)$-alkylene, phenyl, pyrrolyl, imidazolyl, thiazolyl, azetidinyl, thienyl, piperidinyl, pyrrolidinyl, morpholinyl, pyridyl and furyl in which cycloalkyl, phenyl, pyrrolyl, imidazolyl, thiazolyl, azetidinyl, thienyl, piperidinyl, pyrrolidinyl, morpholinyl, pyridyl and furyl may in each case be substituted up to twice by Cl, F, CN, $CF_3$, $OCF_3$, COO—(PG-1), COO—($C_1$–$C_6$)-alkyl, CON—(PG-2)$_2$, CONH—($C_1$–$C_6$)-alkyl, CON—[($C_1$–$C_6$)-alkyl]$_2$, ($C_1$–$C_6$)-alkyl, O—(PG-3), or O—($C_1$–$C_6$)-alkyl, in which PG-3 is a generally known protective group for alcohols, such as, for example, benzyl, allyl, tetrahydropyranyl or tetrahydrofuranyl, and LG is a generally known leaving group such as, for example, halogen, arylsulfonyloxy or alkylsulfonyloxy.

Compounds of the formula (II) are reacted with anilines of the formula (III), which include:

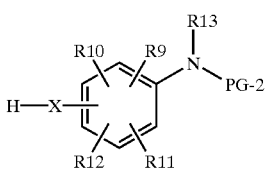

(III)

in which X and PG-2 have the meaning described above, and

R9, R10, R11, R12 are, independently of one another H, F, Cl, Br, O—(PG-3), $CF_3$, $NO_2$, CN, $OCF_3$, O—($C_1$–$C_6$)-alkyl, O—($C_1$–$C_6$)-alkenyl, O—($C_1$–$C_6$)-alkynyl, S—($C_1$–$C_6$)-alkyl, S—($C_1$–$C_6$)-alkenyl, S—($C_1$–$C_6$)-alkynyl, SO—($C_1$–$C_6$)-alkyl, $SO_2$—($C_1$–$C_6$)-alkyl, $SO_2$—N—(PG-2)$_2$, ($C_1$–$C_6$)-alkyl, ($C_1$–$C_6$)-alkenyl, ($C_1$–$C_6$)-alkynyl, ($C_3$–$C_7$)-cycloalkyl, ($C_3$–$C_7$)-cycloalkyl-($C_1$–$C_4$)-alkylene, COO—(PG-1), COO($C_1$–$C_6$)-alkyl, CON—(PG-2)$_2$, CONH($C_1$–$C_6$)-alkyl, CON[($C_1$–$C_6$)-alkyl]$_2$, CONH($C_3$–$C_7$)-cycloalkyl, N—(PG-2)$_2$, NH($C_1$–$C_6$)-alkyl, N[($C_1$–$C_6$)-alkyl]$_2$, NH—CO—($C_1$–$C_6$)-alykl, NH—CO-phenyl, or NH—$SO_2$-phenyl, it being possible for the phenyl ring to be substituted up to twice by F, Cl, CN, O—(PG-3), ($C_1$–$C_6$)-alkyl, O—($C_1$–$C_6$)-alkyl, $CF_3$, $OCF_3$, COO—(PG-1), or COO($C_1$–$C_6$)-alkyl or CON—(PG-2)$_2$;

R13 is H, ($C_1$–$C_6$)-alkyl, O—($C_1$–$C_6$)-alkyl, CO—($C_1$–$C_6$)-alkyl, COO—($C_1$–$C_6$)-alkyl, ($C_1$–$C_6$)-alkylene-COO—(PG-1), or ($C_1$–$C_6$)-alkylene-COO—($C_1$–$C_6$)-alkyl, where PG-1, PG-2 and PG-3 have the meaning described above.

Compounds of the formula (II) react with compounds of the formula (III) in the presence of a base such as, for example, potassium or cesium carbonate, in an organic solvent such as, for example, acetone or dimethylformamide, to give compounds of the formula (IV):

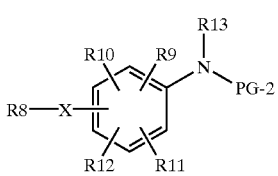

(IV)

in which X, R8, R9, R10, R11, R12, R13 and PG-2 have the meaning described above, the reaction times are between 2 and 24 hours and the reaction temperature is between about 10° C. and the boiling point of the solvent used.

Selective elimination of the protective group PG-2 produces compounds of the formula (V):

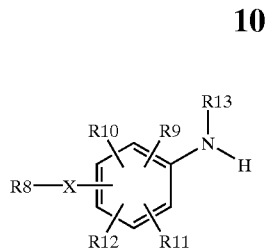

(V)

in which X, R8, R9, R10, R11, R12, and R13 have the meanings stated above.

Compounds of the formula (V) are reacted with isocyanates of the formula (VI), which include:

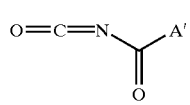

(VI)

in which

A' is phenyl, or naphthyl, it being possible for the phenyl or naphthyl radical to be substituted up to three times by F, Cl, Br, O—(PG-3), $CF_3$, $NO_2$, CN, $OCF_3$, O—($C_1$–$C_6$)-alkyl, O—($C_1$–$C_6$)-alkenyl, O—($C_1$–$C_6$)-alkynyl, S—($C_1$–$C_6$)-alkyl, S—($C_1$–$C_6$)-alkenyl, S—($C_1$–$C_6$)-alkynyl, SO—($C_1$–$C_6$)-alkyl, $SO_2$—($C_1$–$C_6$)-alkyl, $SO_2$—N—(PG-2)$_2$, ($C_1$–$C_6$)-alkyl, ($C_1$–$C_6$)-alkenyl, ($C_1$–$C_6$)-alkynyl, ($C_3$–$C_7$)-cycloalkyl, ($C_3$–$C_7$)-cycloalkyl-($C_1$–$C_4$)-alkylene, ($C_0$–$C_6$)-alkylene-COO—(PG-1), ($C_0$–$C_6$)-alkylene-COO($C_1$–$C_6$)-alkyl, CON—(PG-2)$_2$, CONH($C_1$–$C_6$)-alkyl, CON[($C_1$–$C_6$)-alkyl]$_2$, CONH($C_3$–$C_7$)-cycloalkyl, ($C_0$–$C_6$)-alkylene-N—(PG-2)$_2$, ($C_0$–$C_6$)-alkylene-NH($C_1$–$C_6$)-alkyl, ($C_0$–$C_6$)-alkylene-N[($C_1$–$C_6$)-alkyl]$_2$, NH—CO—($C_1$–$C_6$)-alkyl, NH—CO-phenyl, or NH—$SO_2$-phenyl, it being possible for the phenyl ring to be substituted up to twice by F, Cl, CN, O—(PG-3), ($C_1$–$C_6$)-alkyl, O—($C_1$–$C_6$)-alkyl, $CF_3$, $OCF_3$, COO—(PG-1), COO($C_1$–$C_6$)-alkyl or CON—(PG-2)$_2$, where PG-1, PG-2 and PG-3 have the meanings described above.

The reaction of compounds of formula (V) with isocyanates of the formula (VI) can be carried out in anhydrous organic solvents such as, for example, benzene, toluene or acetonitrile, under a protective gas atmosphere, at reaction temperatures between about 10° C. and the boiling point of the solvent employed, to give compounds of the formula (VII):

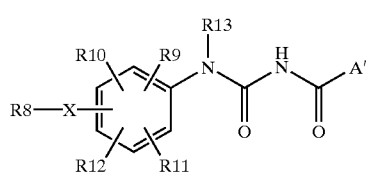

(VII)

in which X, R8, R9, R10, R11, R12, R13 and A' have the meanings described above.

The compounds of the formula (VII) can, if R1 in compounds of the formula (I) is not a hydrogen atom, be alkylated by reaction with compounds of the formula (VII). Compounds of the formula (VII) include:

R14—LG (VIII)

in which LG has the meaning described above, and

R14 is H, (C₁-C₆)-alkyl, O—(C₁-C₆)-alkyl, CO—(C₁-C₆)-alkyl, COO—(C₁-C₆)-alkyl, (C₁-C₆)-alkylene-COO—(PG-1), (C₁-C₆)-alkylene-COO—(C₁-C₆)-alkyl where PG-1 has the meaning described above.

The reaction of compounds of formula (VII) with compounds of formula (VIII) can be carried out in the presence of a base such as, for example, 1,8-diazabicyclo[5.4.0] undec-7-ene, in organic solvents such as, for example, dichloromethane or acetonitrile, to give compounds of the formula (IX):

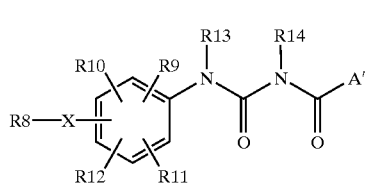
(IX)

which X, R8, R9, R10, R11, R12, R13, R14 and A' have the meanings described above.

After elimination, as disclosed in the literature, of all protective groups, which may be present in the radicals R8, R9, R10, R11, R12, R13, R14, A' and B', compounds of the formula (I) are obtained. Conversion of compounds of the formula (I) into their salts takes place by adding one equivalent of the compound of formula (I) to the appropriate acid or base in an organic solvent such as, for example, acetonitrile or dioxane or in water and by subsequent removal of the solvent.

Another possibility for preparing compounds of the formula (I), in which R2 is a hydrogen atom, is depicted in the following scheme:

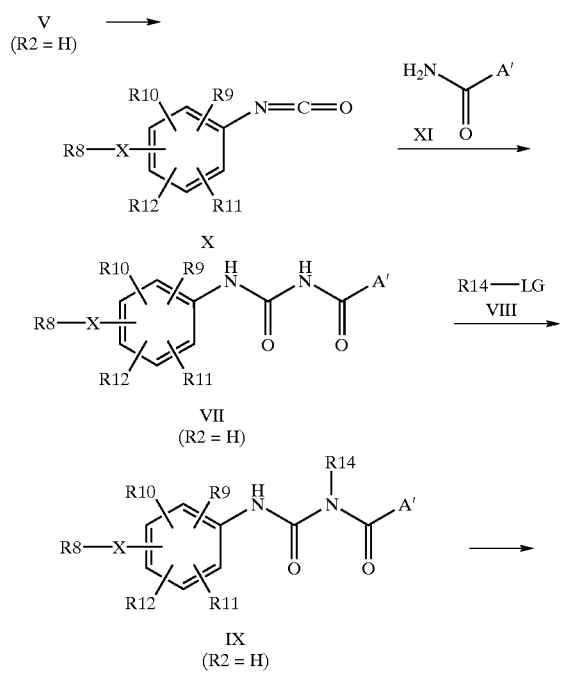

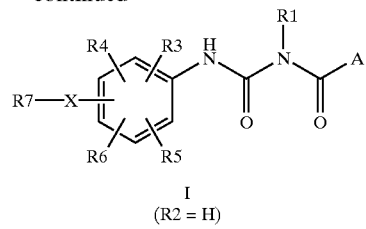
I
(R2 = H)

This route entails converting compounds of the formula (V):

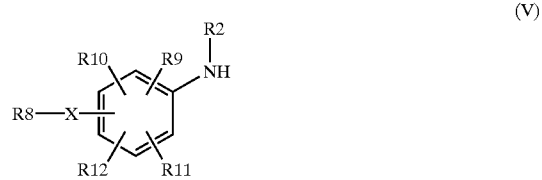
(V)

in which R2 is a hydrogen atom, and X, R8, R9, R10, R11 and R12 have the meanings described above, into isocyanates of the formula (X):

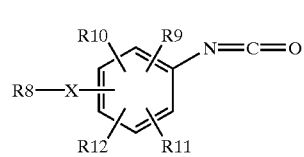
(X)

The reaction between compounds of formula (V) and isocyanates of the formula (X) can be carried out by known methods such as, for example, a reaction with oxalyl chloride in organic solvents such as, for example, 1,2-dichlorethane or dichloromethane, at reaction temperatures between room temperature and the boiling point of the solvent.

Reacting the isocyanates of the formula (X) with amides of the formula (XI):

(XI)

in which A' has the meaning described above, results in compounds of the formula (VII):

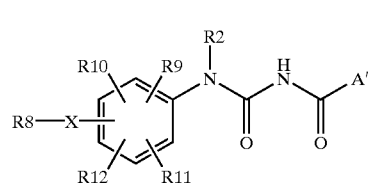
(VII)

in which R2 is a hydrogen atom, and X, R8, R9, R10, R11 and R12 have the meaning described above.

Compounds of the formula (VII) can, if R1 is not a hydrogen atom, be converted as already described above by alkylation with compounds of the formula (VIII) into compounds of the formula (IX), and, if necessary, by subsequent elimination of the protective groups into compounds of the formula (I). Conversion of compounds of the formula (I) into their salts takes place by adding one equivalent of the appropriate acid or base in an organic solvent such as, for example, acetonitrile or dioxane or in water and by subsequent removal of the solvent.

The examples listed hereinafter serve to illustrate the invention without, however, restricting it. The measured solidification or decomposition points (m.p.) have not been corrected and generally depend on the heating rate.

TABLE 1

Examples — Formula (I)

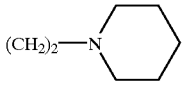

| Ex. | A | R1 | R2 | R3 | R4 | R5 | R6 | R7 | X | Salt | m.p. [° C.] | MS* |
|---|---|---|---|---|---|---|---|---|---|---|---|---|
| 1 | phenyl-2-Cl | H | H | 2-H | 3-Cl | 6-H | 5-Cl | (CH$_2$)$_5$—COOH | 4-O | — | 164 | ok |
| 2 | phenyl-2-Cl | H | H | 2-H | 3-Cl | 6-H | 5-Cl | (CH$_2$)$_5$—COONa | 4-O | — | 177–179 | ok |
| 3 | phenyl-2-Cl | H | H | 2-H | 3-Cl | 6-H | 5-Cl | (CH$_2$)$_5$—COOH | 4-O | bis-2-hydroxy-ethylamine |  | ok |
| 4 | phenyl-2-Cl | H | H | 2-H | 3-Cl | 6-H | 5-Cl | (CH$_2$)$_5$—COOH | 4-O | 3-hydroxy-1-(2-hydroxyethyl)-1-hydroxymethyl-propylamine | 163–165 | ok |
| 5 | phenyl-2-Cl | H | H | 2-H | 3-Cl | 6-H | 5-Cl | (CH$_2$)$_5$—COOH | 4-O | lysine | 170–172 | ok |
| 6 | phenyl-2-Cl | H | H | 2-H | 3-Cl | 6-H | 5-H | CH$_2$COOCH$_3$ | 4-S | — | 168–169 | ok |
| 7 | phenyl-2,6-F$_2$ | H | H | H | H | H | H | CH$_2$COOCH$_3$ | 4-S | — | 152 | ok |
| 8 | phenyl | H | H | H | H | H | H | 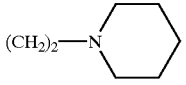 | 4-O | fumaric acid | 182 | ok |
| 9 | phenyl | CH$_3$ | H | H | H | H | H | 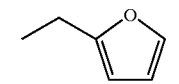 | 4-O | HCl | 82 | ok |
| 10 | phenyl-2-Cl | H | COCH$_3$ | 2-H | 3-Cl | 6-H | 5-Cl | (CH$_2$)$_5$—COOH | 4-O | — | 137–139 | ok |
| 11 | phenyl | H | H | 2-H | 3-Cl | 6-H | 5-Cl | (CH$_2$)$_5$—COOH | 4-O | — | 189–191 | ok |
| 12 | phenyl-2,4-Cl$_2$ | H | H | 2-H | 3-Cl | 6-H | 5-Cl | (CH$_2$)$_5$—COOH | 4-O | — | 202–204 | ok |
| 13 | phenyl-2-Cl | H | H | 2-H | 3-Cl | 6-H | 5-Cl | (CH$_2$)$_5$—COOC$_2$H$_5$ | 4-O | — | 119–121 | ok |
| 14 | phenyl-4-OCH$_3$ | H | H | 2-H | 3-Cl | 6-H | 5-Cl | (CH$_2$)$_5$—COOH | 4-O | — | 188–190 | ok |
| 15 | phenyl-3-F | H | H | 2-H | 3-Cl | 6-H | 5-Cl | (CH$_2$)$_5$—COOH | 4-O | — | 210–214 | ok |
| 16 | phenyl-2-F | H | H | 2-H | 3-Cl | 6-H | 5-Cl | (CH$_2$)$_5$—COOH | 4-O | — | 147–151 | ok |
| 17 | phenyl-2-OCH$_3$ | H | H | 2-H | 3-Cl | 6-H | 5-Cl | (CH$_2$)$_5$—COOH | 4-O | — | 149–153 | ok |
| 18 | phenyl-2,3-Cl$_2$ | H | H | 2-H | 3-Cl | 6-H | 5-Cl | (CH$_2$)$_5$—COOH | 4-O | — | 170–172 | ok |
| 19 | phenyl-2-F | H | H | H | H | H | H | 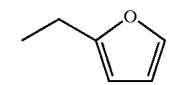 | 4-S | — | 139–143 |  |
| 20 | phenyl-2,6-F$_2$ | H | H | H | H | H | H | 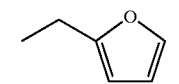 | 4-S | — | 162–163 |  |
| 21 | phenyl-2,6-F$_2$ | H | H | 2-H | 3-Cl | 6-H | 5-Cl |  | 4-S | — | 152 |  |
| 22 | phenyl-2-Cl | H | H | H | H | H | H | CH$_2$—COOCH$_3$ | 4-S | — | 125–126 |  |
| 23 | phenyl-3-OCH$_3$ | H | H | 2-H | 3-Cl | 6-H | 5-Cl | (CH$_2$)$_5$—COOH | 4-O | — | 136 | ok |

TABLE 1-continued

| | | | | | | | | | | | |
|---|---|---|---|---|---|---|---|---|---|---|---|
| 24 | phenyl-2,4-Cl$_2$ | H | H | 2-H | 3-Cl | 6-H | 5-Cl | 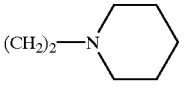(CH$_2$)$_2$—N(piperidine) | 4-O | — | 189 | ok |
| 25 | phenyl-3-F | H | H | 2-H | 3-Cl | 6-H | 5-Cl | 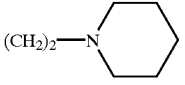(CH$_2$)$_2$—N(piperidine) | 4-O | — | 204 | ok |
| 26 | phenyl-2,3-Cl$_2$ | H | H | 2-H | 3-Cl | 6-H | 5-Cl | 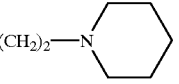(CH$_2$)$_2$—N(piperidine) | 4-O | — | 182 | ok |
| 27 | phenyl-3-OCH$_3$ | H | H | 2-H | 3-Cl | 6-H | 5-Cl | 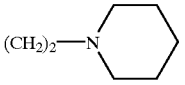(CH$_2$)$_2$—N(piperidine) | 4-O | — | 176 | ok |
| 28 | phenyl-2-F | H | H | 2-H | 3-Cl | 6-H | 5-Cl | 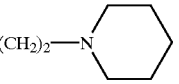(CH$_2$)$_2$—N(piperidine) | 4-O | — | 144 | ok |
| 29 | phenyl | H | H | 2-H | 3-Cl | 6-H | 5-Cl | 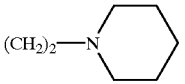(CH$_2$)$_2$—N(piperidine) | 4-O | — | 204 | ok |
| 30 | phenyl-4-OCH$_3$ | H | H | 2-H | 3-Cl | 6-H | 5-Cl | 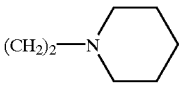(CH$_2$)$_2$—N(piperidine) | 4-O | TFA | | ok |
| 31 | phenyl-2-OCH$_3$ | H | H | 2-H | 3-Cl | 6-H | 5-Cl | 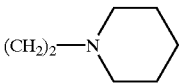(CH$_2$)$_2$—N(piperidine) | 4-O | TFA | | ok |
| 32 | phenyl-2-Cl | H | H | 2-H | 3-Cl | 6-H | 5-Cl | (CH$_2$)$_3$—COOH | 4-O | — | | ok |
| 33 | phenyl-2-Cl | H | H | 2-H | 3-Cl | 6-H | 5-Cl | (CH$_2$)$_4$—COOH | 4-O | — | | ok |
| 34 | phenyl-2-Cl | H | H | 2-H | 3-Cl | 6-H | 5-Cl | (CH$_2$)$_6$—COOH | 4-O | — | | ok |
| 35 | phenyl-2-Cl | H | H | 2-H | 3-Cl | 6-H | 5-Cl | (CH$_2$)$_7$—COOH | 4-O | — | | ok |
| 36 | phenyl-2-Cl | CH$_3$ | H | 2-H | 3-Cl | 6-H | 5-Cl | (CH$_2$)$_5$—COOH | 4-O | — | | ok |
| 37 | phenyl-2-Cl | H | H | 2-H | 3-Cl | 6-H | 5-Cl | (CH$_2$)$_3$—COOH | 4-O | 3-hydroxy-1-(2-hydroxyethyl)-1-hydroxymethyl-propylamine | | ok |
| 38 | phenyl-2-Cl | H | H | 2-H | 3-Cl | 6-H | 5-Cl | (CH$_2$)$_4$—COOH | 4-O | 3-hydroxy-1-(2-hydroxyethyl)-1-hydroxymethyl-propylamine | | ok |
| 39 | phenyl-2-Cl | H | H | 2-H | 3-Cl | 6-H | 5-Cl | (CH$_2$)$_6$—COOH | 4-O | 3-hydroxy-1-(2-hydroxyethyl)-1-hydroxymethyl-propylamine | | ok |
| 40 | phenyl-2-Cl | H | H | 2-H | 3-Cl | 6-H | 5-Cl | (CH$_2$)$_7$—COOH | 4-O | 3-hydroxy-1-(2-hydroxyethyl)-1-hydroxymethyl-propylamine | | ok |
| 41 | phenyl-2,4-Cl$_2$ | H | H | 2-H | 3-Cl | 6-H | 5-Cl | (CH$_2$)$_3$—COOH | 4-O | 3-hydroxy-1-(2-hydroxyethyl)-1-hydroxymethyl-propylamine | | ok |
| 42 | phenyl-2,4-Cl$_2$ | H | H | 2-H | 3-Cl | 6-H | 5-Cl | (CH$_2$)$_4$—COOH | 4-O | 3-hydroxy-1-(2-hydroxyethyl)-1-hydroxymethyl-propylamine | | ok |
| 43 | phenyl-2,4-Cl$_2$ | H | H | 2-H | 3-Cl | 6-H | 5-Cl | (CH$_2$)$_6$—COOH | 4-O | 3-hydroxy-1-(2-hydroxyethyl)-1-hydroxymethyl-propylamine | | ok |
| 44 | phenyl-2,4-Cl$_2$ | H | H | 2-H | 3-Cl | 6-H | 5-Cl | (CH$_2$)$_7$—COOH | 4-O | 3-hydroxy-1-(2-hydroxyethyl)-1-hydroxymethyl-propylamine | | ok |

TABLE 1-continued

| # | | | | | | | | | | | | |
|---|---|---|---|---|---|---|---|---|---|---|---|---|
| 45 | phenyl-2-Cl | H | H | 2-H | 3-Cl | 6-H | 5-Cl | (CH$_2$)$_3$—N(piperidine) 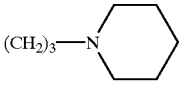 | 4-O | HCl | | ok |
| 46 | phenyl-2,4-Cl$_2$ | H | H | 2-H | 3-Cl | 6-H | 5-Cl | (CH$_2$)$_3$—N(piperidine) 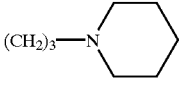 | 4-O | HCl | 182 | ok |
| 47 | phenyl-2-CH$_3$ | H | H | 2-H | 3-Cl | 6-H | 5-Cl | (CH$_2$)$_5$—COOH | 4-O | 3-hydroxy-1-(2-hydroxyethyl)-1-hydroxymethyl-propylamine | | ok |
| 48 | phenyl-4-CH$_3$ | H | H | 2-H | 3-Cl | 6-H | 5-Cl | (CH$_2$)$_5$—COOH | 4-O | 3-hydroxy-1-(2-hydroxyethyl)-1-hydroxymethyl-propylamine | | ok |
| 49 | phenyl-3-CH$_3$ | H | H | 2-H | 3-Cl | 6-H | 5-Cl | (CH$_2$)$_5$—COOH | 4-O | 3-hydroxy-1-(2-hydroxyethyl)-1-hydroxymethyl-propylamine | | ok |
| 50 | phenyl-4-F | H | H | 2-H | 3-Cl | 6-H | 5-Cl | (CH$_2$)$_5$—COOH | 4-O | 3-hydroxy-1-(2-hydroxyethyl)-1-hydroxymethyl-propylamine | | ok |
| 51 | phenyl-3-Cl | H | H | 2-H | 3-Cl | 6-H | 5-Cl | (CH$_2$)$_5$—COOH | 4-O | 3-hydroxy-1-(2-hydroxyethyl)-1-hydroxymethyl-propylamine | | ok |
| 52 | phenyl-2-Cl | H | H | 2-H | 3-Cl | 6-H | 5-Cl | (CH$_2$)$_5$—COOK | 4-O | — | | ok |
| 53 | phenyl-4-Br | H | H | 2-H | 3-Cl | 6-H | 5-Cl | (CH$_2$)$_5$—COOH | 4-O | 3-hydroxy-1-(2-hydroxyethyl)-1-hydroxymethyl-propylamine | | ok |
| 54 | phenyl | H | H | 2-H | 3-Cl | 6-H | 5-Cl | (CH$_2$)$_5$—COOH | 4-O | 3-hydroxy-1-(2-hydroxyethyl)-1-hydroxymethyl-propylamine | 172 | ok |
| 55 | phenyl-3-F | H | H | 2-H | 3-Cl | 6-H | 5-Cl | (CH$_2$)$_5$—COOH | 4-O | 3-hydroxy-1-(2-hydroxyethyl)-1-hydroxymethyl-propylamine | 170 | ok |
| 56 | phenyl-2-OCH$_3$ | H | H | 2-H | 3-Cl | 6-H | 5-Cl | (CH$_2$)$_5$—COOH | 4-O | 3-hydroxy-1-(2-hydroxyethyl)-1-hydroxymethyl-propylamine | 119 | ok |
| 57 | phenyl-2,3-Cl$_2$ | H | H | 2-H | 3-Cl | 6-H | 5-Cl | (CH$_2$)$_5$—COOH | 4-O | 3-hydroxy-1-(2-hydroxyethyl)-1-hydroxymethyl-propylamine | 160 | ok |
| 58 | phenyl-4-Cl | H | H | 2-H | 3-Cl | 6-H | 5-Cl | (CH$_2$)$_5$—COOH | 4-O | 3-hydroxy-1-(2-hydroxyethyl)-1-hydroxymethyl-propylamine | | ok |
| 59 | phenyl-2,4-Cl$_2$ | H | H | 2-H | 3-Cl | 6-H | 5-Cl | (CH$_2$)$_5$—COOH | 4-O | 3-hydroxy-1-(2-hydroxyethyl)-1-hydroxymethyl-propylamine | | ok |
| 60 | phenyl-2-CH$_3$ | H | H | 2-H | 3-Cl | 6-H | 5-Cl | (CH$_2$)$_3$—COOH | 4-O | — | 207 | ok |
| 61 | phenyl-2-CH$_3$ | H | H | 2-H | 3-Cl | 6-H | 5-Cl | (CH$_2$)$_4$—COOH | 4-O | — | 167 | ok |
| 62 | phenyl-2-CH$_3$ | H | H | 2-H | 3-Cl | 6-H | 5-Cl | (CH$_2$)$_6$—COOH | 4-O | — | 185 | ok |
| 63 | phenyl-2-CH$_3$ | H | H | 2-H | 3-Cl | 6-H | 5-Cl | (CH$_2$)$_7$—COOH | 4-O | — | 153 | ok |
| 64 | phenyl-2,4-Cl$_2$ | H | H | 2-H | 3-F | 6-H | 5-H | (CH$_2$)$_3$—COOH | 4-O | — | | ok |
| 65 | phenyl-2,4-Cl$_2$ | H | H | 2-H | 3-F | 6-H | 5-H | (CH$_2$)$_4$—COOH | 4-O | — | | ok |
| 66 | phenyl-2,4-Cl$_2$ | H | H | 2-H | 3-F | 6-H | 5-H | (CH$_2$)$_5$—COOH | 4-O | — | | ok |
| 67 | phenyl-2,4-Cl$_2$ | H | H | 2-H | 3-F | 6-H | 5-H | (CH$_2$)$_6$—COOH | 4-O | — | | ok |
| 68 | phenyl-2,4-Cl$_2$ | H | H | 2-H | 3-F | 6-H | 5-H | (CH$_2$)$_7$—COOH | 4-O | — | | ok |
| 69 | phenyl-2,4- | H | H | 2-CH$_3$ | 4-H | 6-H | 5-H | (CH$_2$)$_3$—COOH | 3-O | — | | ok |

TABLE 1-continued

| | | | | | | | | | | | |
|---|---|---|---|---|---|---|---|---|---|---|---|
| 70 | phenyl-2,4-Cl$_2$ | H | H | 2-CH$_3$ | 4-H | 6-H | 5-H | (CH$_2$)$_4$—COOH | 3-O | — | ok |
| 71 | phenyl-2,4-Cl$_2$ | H | H | 2-CH$_3$ | 4-H | 6-H | 5-H | (CH$_2$)$_5$—COOH | 3-O | — | ok |
| 72 | phenyl-2,4-Cl$_2$ | H | H | 2-CH$_3$ | 4-H | 6-H | 5-H | (CH$_2$)$_6$—COOH | 3-O | — | ok |
| 73 | phenyl-2,4-Cl$_2$ | H | H | 2-CH$_3$ | 4-H | 6-H | 5-H | (CH$_2$)$_7$—COOH | 3-O | — | ok |
| 74 | phenyl-2,4-Cl$_2$ | H | H | 2-CH$_3$ | 3-H | 6-H | 5-H | (CH$_2$)$_3$—COOH | 4-O | — | ok |
| 75 | phenyl-2,4-Cl$_2$ | H | H | 2-CH$_3$ | 3-H | 6-H | 5-H | (CH$_2$)$_4$—COOH | 4-O | — | ok |
| 76 | phenyl-2,4-Cl$_2$ | H | H | 2-CH$_3$ | 3-H | 6-H | 5-H | (CH$_2$)$_5$—COOH | 4-O | — | ok |
| 77 | phenyl-2,4-Cl$_2$ | H | H | 2-CH$_3$ | 3-H | 6-H | 5-H | (CH$_2$)$_6$—COOH | 4-O | — | ok |
| 78 | phenyl-2,4-Cl$_2$ | H | H | 2-CH$_3$ | 3-H | 6-H | 5-H | (CH$_2$)$_7$—COOH | 4-O | — | ok |
| 79 | phenyl-2,4-Cl$_2$ | H | H | 2-H | 3-CH$_3$ | 6-H | 5-CH$_3$ | (CH$_2$)$_3$—COOH | 4-O | — | ok |
| 80 | phenyl-2,4-Cl$_2$ | H | H | 2-H | 3-CH$_3$ | 6-H | 5-CH$_3$ | (CH$_2$)$_4$—COOH | 4-O | — | ok |
| 81 | phenyl-2,4-Cl$_2$ | H | H | 2-H | 3-CH$_3$ | 6-H | 5-CH$_3$ | (CH$_2$)$_5$—COOH | 4-O | — | ok |
| 82 | phenyl-2,4-Cl$_2$ | H | H | 2-H | 3-CH$_3$ | 6-H | 5-CH$_3$ | (CH$_2$)$_6$—COOH | 4-O | — | ok |
| 83 | phenyl-2,4-Cl$_2$ | H | H | 2-H | 3-CH$_3$ | 6-H | 5-CH$_3$ | (CH$_2$)$_7$—COOH | 4-O | — | ok |
| 84 | phenyl-2,4-Cl$_2$ | H | H | H | H | H | H | (CH$_2$)$_3$—COOH | 3-O | — | ok |
| 85 | phenyl-2,4-Cl$_2$ | H | H | H | H | H | H | (CH$_2$)$_4$—COOH | 3-O | — | ok |
| 86 | phenyl-2,4-Cl$_2$ | H | H | H | H | H | H | (CH$_2$)$_5$—COOH | 3-O | — | ok |
| 87 | phenyl-2,4-Cl$_2$ | H | H | H | H | H | H | (CH$_2$)$_7$—COOH | 3-O | — | ok |
| 88 | phenyl-2,4-Cl$_2$ | H | H | H | H | H | H | (CH$_2$)$_3$—COOH | 4-O | — | ok |
| 89 | phenyl-2,4-Cl$_2$ | H | H | H | H | H | H | (CH$_2$)$_4$—COOH | 4-O | — | ok |
| 90 | phenyl-2,4-Cl$_2$ | H | H | H | H | H | H | (CH$_2$)$_5$—COOH | 4-O | — | ok |
| 91 | phenyl-2,4-Cl$_2$ | H | H | H | H | H | H | (CH$_2$)$_6$—COOH | 4-O | — | ok |
| 92 | phenyl-2,4-Cl$_2$ | H | H | H | H | H | H | (CH$_2$)$_7$—COOH | 4-O | — | ok |
| 93 | phenyl-3,4-Cl$_2$ | H | H | 2-H | 3-Cl | 6-H | 5-Cl | (CH$_2$)$_5$—COOH | 4-O | — | ok |
| 94 | phenyl-2,4-Cl$_2$ | H | H | 2-H | 3-Cl | 6-H | 5-Cl | 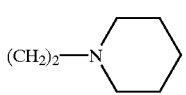 | 4-O | HCl | ok |
| 95 | phenyl-3-F | H | H | 2-H | 3-Cl | 6-H | 5-Cl | 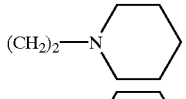 | 4-O | HCl | ok |
| 96 | phenyl-2,3-Cl$_2$ | H | H | 2-H | 3-Cl | 6-H | 5-Cl | 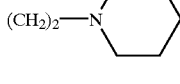 | 4-O | HCl | ok |
| 97 | phenyl-3-OCH$_3$ | H | H | 2-H | 3-Cl | 6-H | 5-Cl | 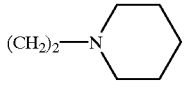 | 4-O | HCl | ok |
| 98 | phenyl-2-F | H | H | 2-H | 3-Cl | 6-H | 5-Cl | 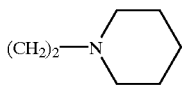 | 4-O | HCl | ok |
| 99 | phenyl | H | H | 2-H | 3-Cl | 6-H | 5-Cl | 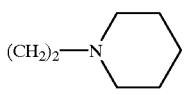 | 4-O | HCl | ok |

TABLE 1-continued

| | | | | | | | | | | |
|---|---|---|---|---|---|---|---|---|---|---|
| 100 | phenyl-3-SO$_2$CH$_3$ | H | H | 2-H | 3-Cl | 6-H | 5-Cl | (CH$_2$)$_5$—COOH | 4-O | — | ok |
| 101 | phenyl-2-SO$_2$CH$_3$ | H | H | 2-H | 3-Cl | 6-H | 5-Cl | (CH$_2$)$_5$—COOH | 4-O | — | ok |
| 102 | phenyl-2-Cl-4-SO$_2$CH$_3$ | H | H | 2-H | 3-Cl | 6-H | 5-Cl | (CH$_2$)$_5$—COOH | 4-O | — | ok |
| 103 | phenyl-2,4-(CH$_3$)$_2$ | H | H | 2-H | 3-Cl | 6-H | 5-Cl | (CH$_2$)$_5$—COOH | 4-O | — | ok |
| 104 | phenyl-4-Cl-2-F | H | H | 2-H | 3-Cl | 6-H | 5-Cl | (CH$_2$)$_5$—COOH | 4-O | — | ok |
| 105 | phenyl-2-Cl-4-F | H | H | 2-H | 3-Cl | 6-H | 5-Cl | (CH$_2$)$_5$—COOH | 4-O | — | ok |
| 106 | phenyl-4-COOCH$_3$ | H | H | 2-H | 3-Cl | 6-H | 5-Cl | (CH$_2$)$_5$—COOH | 4-O | — | ok |
| 107 | phenyl-4-SO$_2$CH$_3$ | H | H | 2-H | 3-Cl | 6-H | 5-Cl | (CH$_2$)$_5$—COOH | 4-O | — | ok |
| 108 | phenyl-2-Cl | H | H | 2-H | 3-Cl | 6-H | 5-Cl | 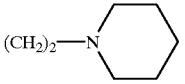 | 4-O | — | ok |
| 109 | phenyl-4-Cl-2-CH$_3$ | H | H | 2-H | 3-Cl | 6-H | 5-Cl | (CH$_2$)$_5$—COOH | 4-O | — | ok |
| 110 | phenyl-3-F-4-NO$_2$ | H | H | 2-H | 3-Cl | 6-H | 5-Cl | (CH$_2$)$_5$—COOH | 4-O | — | ok |
| 111 | phenyl-2-COOCH$_3$ | H | H | 2-H | 3-Cl | 6-H | 5-Cl | (CH$_2$)$_5$—COOH | 4-O | — | ok |
| 112 | phenyl-3-COOCH$_3$-5-NO$_2$ | H | H | 2-H | 3-Cl | 6-H | 5-Cl | (CH$_2$)$_5$—COOH | 4-O | — | ok |
| 113 | phenyl-3-CF$_3$ | H | H | 2-H | 3-Cl | 6-H | 5-Cl | (CH$_2$)$_5$—COOH | 4-O | — | ok |
| 114 | phenyl-2,4-Cl$_2$ | H | H | H | H | H | H | (CH$_2$)$_6$—COOH | 3-O | — | ok |
| 115 | phenyl-2,4-Cl$_2$ | H | H | 2-H | 3-Cl | 6-H | 5-H | (CH$_2$)$_4$—COOH | 4-O | — | ok |
| 116 | phenyl-2,4-Cl$_2$ | H | H | 2-F | 3-H | 6-H | 5-H | (CH$_2$)$_5$—COOH | 4-O | — | ok |
| 117 | phenyl-4-CF$_3$ | H | H | 2-H | 3-Cl | 6-H | 5-Cl | (CH$_2$)$_5$—COOH | 4-O | — | ok |
| 118 | phenyl-2-Cl | H | H | 2-H | 3-Cl | 6-H | 5-Cl | (CH$_2$)$_5$—CONH$_2$ | 4-O | — | ok |
| 119 | phenyl-2,4-Cl$_2$ | H | H | 2-CH$_3$ | 3-H | 6-CH$_3$ | 5-H | (CH$_2$)$_4$—COOH | 4-O | — | ok |
| 120 | phenyl-2,4-Cl$_2$ | H | H | 2-H | 4-CH$_3$ | 6-H | 5-H | (CH$_2$)$_4$—COOH | 3-O | — | ok |
| 121 | phenyl-2,4-Cl$_2$ | H | H | 2-H | 4-OCH$_3$ | 6-H | 5-H | (CH$_2$)$_4$—COOH | 3-O | — | ok |
| 122 | phenyl-2,4-Cl$_2$ | H | H | 2-H | 3-COOCH$_3$ | 6-H | 5-H | (CH$_2$)$_4$—COOH | 4-O | — | ok |
| 123 | phenyl-2,4-Cl$_2$ | H | H | 2-Cl | 3-H | 6-H | 5-H | (CH$_2$)$_4$—COOH | 4-O | — | ok |
| 124 | phenyl-2,4-Cl$_2$ | H | H | 2-H | 3-cHexyl | 6-H | 5-H | (CH$_2$)$_4$—COOH | 4-O | — | ok |
| 125 | phenyl-2,4-Cl$_2$ | H | H | 2-CH$_3$ | 3-CH$_3$ | 6-H | 5-H | (CH$_2$)$_4$—COOH | 4-O | — | ok |
| 126 | phenyl-2,4-Cl$_2$ | H | H | 2-CH$_3$ | 3-H | 6-CH$_3$ | 5-H | (CH$_2$)$_5$—COOH | 4-O | — | ok |
| 127 | phenyl-2,4-Cl$_2$ | H | H | 2-H | 4-CH$_3$ | 6-H | 5-H | (CH$_2$)$_5$—COOH | 3-O | — | ok |
| 128 | phenyl-2,4-Cl$_2$ | H | H | 2-H | 4-OCH$_3$ | 6-H | 5-H | (CH$_2$)$_5$—COOH | 3-O | — | ok |
| 129 | phenyl-2,4-Cl$_2$ | H | H | 2-H | 3-COOCH$_3$ | 6-H | 5-H | (CH$_2$)$_5$—COOH | 4-O | — | ok |
| 130 | phenyl-2,4-Cl$_2$ | H | H | 2-Cl | 3-H | 6-H | 5-H | (CH$_2$)$_5$—COOH | 4-O | — | ok |
| 131 | phenyl-2,4-Cl$_2$ | H | H | 2-H | 3-cHexyl | 6-H | 5-H | (CH$_2$)$_5$—COOH | 4-O | — | ok |
| 132 | phenyl-2,4-Cl$_2$ | H | H | 2-CH$_3$ | 3-H | 6-H | 5-CH$_3$ | (CH$_2$)$_5$—COOH | 4-O | — | ok |
| 133 | phenyl-2,4-Cl$_2$ | H | H | 2-CH$_3$ | 3-CH$_3$ | 6-H | 5-H | (CH$_2$)$_5$—COOH | 4-O | — | ok |
| 134 | phenyl-2,4-Cl$_2$ | H | H | 2-CH$_3$ | 3-H | 6-CH$_3$ | 5-H | (CH$_2$)$_7$—COOH | 4-O | — | ok |
| 135 | phenyl-2,4-Cl$_2$ | H | H | 2-H | 4-CH$_3$ | 6-H | 5-H | (CH$_2$)$_7$—COOH | 3-O | — | ok |
| 136 | phenyl-2,4-Cl$_2$ | H | H | 2-H | 4-OCH$_3$ | 6-H | 5-H | (CH$_2$)$_7$—COOH | 3-O | — | ok |

TABLE 1-continued

| | | | | | | | | | | | |
|---|---|---|---|---|---|---|---|---|---|---|---|
| 137 | phenyl-2,4-Cl$_2$ | H | H | 2-H | 3-COOCH$_3$ | 6-H | 5-H | (CH$_2$)$_7$—COOH | 4-O | — | ok |
| 138 | phenyl-2,4-Cl$_2$ | H | H | 2-Cl | 3-H | 6-H | 5-H | (CH$_2$)$_7$—COOH | 4-O | — | ok |
| 139 | phenyl-2,4-Cl$_2$ | H | H | 2-CH$_3$ | 3-H | 6-H | 5-CH$_3$ | (CH$_2$)$_7$—COOH | 4-O | — | ok |
| 140 | phenyl-2,4-Cl$_2$ | H | H | 2-CH$_3$ | 3-CH$_3$ | 6-H | 5-H | (CH$_2$)$_7$—COOH | 4-O | — | ok |
| 141 | phenyl-2,4-Cl$_2$ | H | H | 2-CH$_3$ | 3-H | 6-CH$_3$ | 5-H | (CH$_2$)$_3$—COOH | 4-O | — | ok |
| 142 | phenyl-2,4-Cl$_2$ | H | H | 2-H | 4-CH$_3$ | 6-H | 5-H | (CH$_2$)$_3$—COOH | 3-O | — | ok |
| 143 | phenyl-2,4-Cl$_2$ | H | H | 2-H | 4-OCH$_3$ | 6-H | 5-H | (CH$_2$)$_3$—COOH | 3-O | — | ok |
| 144 | phenyl-2,4-Cl$_2$ | H | H | 2-H | 3-COOCH$_3$ | 6-H | 5-H | (CH$_2$)$_3$—COOH | 4-O | — | ok |
| 145 | phenyl-2,4-Cl$_2$ | H | H | 2-Cl | 3-H | 6-H | 5-H | (CH$_2$)$_3$—COOH | 4-O | — | ok |
| 146 | phenyl-2,4-Cl$_2$ | H | H | 2-H | 3-cHexyl | 6-H | 5-H | (CH$_2$)$_3$—COOH | 4-O | — | ok |
| 147 | phenyl-2,4-Cl$_2$ | H | H | 2-CH$_3$ | 3-H | 6-H | 5-CH$_3$ | (CH$_2$)$_3$—COOH | 4-O | — | ok |
| 148 | phenyl-2,4-Cl$_2$ | H | H | 2-CH$_3$ | 3-CH$_3$ | 6-H | 5-H | (CH$_2$)$_3$—COOH | 4-O | — | ok |
| 149 | phenyl-2,6-Cl$_2$ | H | H | 2-H | 3-Cl | 6-H | 5-Cl | (CH$_2$)$_5$—COOH | 4-O | — | ok |
| 150 | phenyl-6-Cl-3-COOH | H | H | 2-H | 3-Cl | 6-H | 5-Cl | (CH$_2$)$_3$—COOH | 4-O | — | ok |
| 151 | phenyl-2,4-Cl$_2$ | H | H | 2-CH$_3$ | 4-H | 6-H | 5-H | (CH$_2$)$_4$—COOH | 3-O | bis-2-hydroxy-ethylamine | ok |
| 152 | phenyl-2,4-Cl$_2$ | H | H | 2-Cl | 3-H | 6-H | 5-H | (CH$_2$)$_3$—COOH | 4-O | bis-2-hydroxy-ethylamine | ok |
| 153 | phenyl-2,4-Cl$_2$ | H | H | 2-CH$_3$ | 3-CH$_3$ | 6-H | 5-H | (CH$_2$)$_3$—COOH | 4-O | bis-2-hydroxy-ethylamine | ok |
| 154 | phenyl-2,4-Cl$_2$ | H | H | 2-H | 4-OCH$_3$ | 6-H | 5-H | (CH$_2$)$_2$—N—(C$_2$H$_5$)$_2$ | 3-O | — | ok |
| 155 | phenyl-2,4-Cl$_2$ | H | H | H | H | H | H | (CH$_2$)$_2$—N—(C$_2$H$_5$)$_2$ | 4-O | — | ok |

*The statement MS is "ok" means that a mass spectrum was recorded and the molecular peak (molecular mass + H$^+$) was detected therein.

The compounds of the formula (I) are distinguished by beneficial effects on glucose metabolism; for example, they lower the blood glucose level and are suitable for treating type II diabetes. The compounds can be employed alone or in combination with other blood glucose-lowering active ingredients. Examples of such other blood glucose-lowering active ingredients are sulfonylureas (such as, for example, glimerpiride, glibenclamide), glitazones (such as, for example, troglitazone, rosiglitazone), alpha-glucosidase inhibitors (such as, for example, acarbose, miglitol) or insulins.

The activity of the compounds was assayed as follows:
Glycogen Phosphorylase a Activity Assay The effect of compounds on the activity of the active form of glycogen phosphorylase (GPa) was measured in the reverse direction by following the synthesis of glycogen from glucose 1-phosphate by determining the liberation of inorganic phosphate. All the reactions were carried out as duplicate determinations in microtiter plates with 96 wells (Half Area Plates, Costar No 3696), measuring the change in absorption owing to the formation of the reaction product at the wavelength specified hereinafter in a Multiskan Ascent Elisa Reader (Lab Systems, Finland).

In order to measure the GPa enzymic activity in the reverse direction, the general method of Engers et al. (Engers H D, Shechosky S, Madsen N B, Can J Biochem 1970 July; 48(7):746–754) was used to measure the conversion of glucose 1-phosphate into glycogen and inorganic phosphate. However, the following modifications to Engers method were observed: human glycogen phosphorylase a (for example with about 0.76 mg of protein/ml (Aventis Pharma Deutschland GmbH), was dissolved in buffer solution E (25-mM β-glycerophosphate, pH 7.0, 1 mM EDTA and 1 mM dithiothreitol) and was diluted with buffer T (50 mM hepes, pH 7.0, 100 mM KCl, 2.5 mM EDTA, 2.5 mM MgCl$_2$.6H$_2$O) and addition of 5 mg/ml glycogen to a concentration of 10 μg of protein/ml. Test substances were prepared as 10 mM solutions in DMSO and diluted to 50 μM with buffer solution T. 10 μl of this solution were mixed with 10 μl of 37.5 mM glucose (dissolved in buffer solution T and 5 mg/ml glycogen), 10 μl of a solution of human glycogen phosphorylase a (10 μg of protein /ml), and 20 μl of glucose 1-phosphate, 2,5 mM. The baseline glycogen phosphorylase a activity in the absence of test substance was determined by adding 10 μl of buffer solution T (0.1% DMSO). The mixture was incubated at room temperature for 40 minutes, and the liberated organic phosphate was measured by the general method of Drueckes et al. (Drueckes P, Schinzel R, Palm D, Anal Biochem Sep. 1, 1995; 230(1):173–177) with the following modifications: 50 μl of a stop solution containing 7.3 mM ammonium molybdate, 10.9 mM zinc acetate, 3.6% ascorbic acid, and 0.9% SDS are added to 50 μl of the enzyme mixture. After incubation at 45° C. for 60 minutes, the absorption at 820 nm was measured. In order to determine the background absorption, in a separate mixture, the stop solution was added immediately after addition of the glucose 1-phosphate solution. This test was carried out with a concentration of 10 μM of the test substance in order to determine the particular inhibition of glycogen phosphorylase a in vitro by the test substance.

TABLE 2

Biological activity:

| Ex. | % inhibition at 10 μM |
|---|---|
| 1 | 87 |
| 2 | 73 |
| 3 | 75 |
| 4 | 79 |
| 5 | 77 |
| 12 | 92 |
| 20 | 35 |
| 29 | 78 |
| 30 | 76 |
| 31 | 86 |
| 41 | 50 |
| 44 | 11 |
| 46 | 36 |
| 47 | 46 |
| 49 | 13 |
| 51 | 36 |
| 53 | 22 |
| 60 | 36 |
| 70 | 86 |
| 75 | 41 |
| 80 | 50 |
| 84 | 44 |
| 89 | 90 |
| 90 | 34 |
| 100 | 78 |
| 101 | 93 |
| 102 | 14 |
| 106 | 35 |
| 111 | 88 |
| 112 | 100 |
| 116 | 100 |
| 117 | 99 |
| 118 | 70 |
| 119 | 97 |
| 120 | 40 |
| 122 | 12 |
| 128 | 95 |
| 147 | 88 |
| 149 | 76 |

It is evident from the table that the compounds of the formula (I) inhibit the activity of glycogen phosphorylase a and thus are very suitable for lowering the blood glucose level.

The preparation of some examples is described in detail below, and the other compounds of the formula (I) were obtained analogously:

Experimental Part

EXAMPLE 1

6-{2,6-Dichloro-4-[(2-chlorobenzoyl)ureido]phenoxy}hexanoic Acid a) Ethyl 6-(4-Acetylamino-2,6-dichlorophenoxy)hexanoate 13.3 ml (74.9 mmol) of ethyl 6-bromohexanoate and 52.1 g (160 mmol) of cesium carbonate were added to a solution of 15.0 g (68.1 mmol) of N-(3,5-dichloro-4-hydroxyphenyl)acetamide in 300 ml of acetone. The suspension was boiled under reflux for 8 hours, and then 600 ml of water were added. The mixture was extracted twice with 400 ml of dichloromethane and with 400 ml of MTB ether each time. The combined organic phases were washed with water and concentrated in a rotary evaporator. The product was employed in the next step without purification. Crude yield was 30 g.

b) 6-(4-Acetylamino-2,6-dichlorophenoxy)hexanoic Acid 30 g of crude material from step a) were mixed with 800 ml of 1 M potassium hydroxide solution and stirred at room temperature for 3 days, after which 600 ml of water were added and the pH was adjusted to 5.5 with about 80 ml of glacial acetic acid. The precipitated product was filtered off with suction and washed twice with 40 ml of water each time. The precipitate was dried under high vacuum and produced 14.6 g of the required compound.

c) 6-(4-Amino-2,6-dichlorophenoxy)hexanoic Acid 7.5 g (22.4 mmol) of 6-(4-acetylamino-2,6-dichlorophenoxy)hexanoic acid in 140 ml of 1 m potassium hydroxide solution in methanol/water (3:1) were boiled under reflux overnight. The methanol was removed in a rotary evaporator, and the residue was diluted with about 30 ml of water and acidified to pH 5 with glacial acetic acid. The mixture was stirred in an ice bath for 30 minutes and then filtered with suction. The crude product was subjected to column chromatography using n-heptane/ethyl acetate=1/1 and produced 4.3 g (14.7 mmol, 66%) of the required product.

d) 6-{2,6-Dichloro-4-[(2-chlorobenzoyl)ureido]phenoxy}hexanoic Acid

A solution of 7.5 g (41.1 mmol) of 2-chlorobenzoyl isocyanate in 300 ml of acetonitrile was added to a suspension of 10.0 g (34.2 mmol) of 6-(4-amino-2,6-dichlorophenoxy)hexanoic acid in 700 ml of dry acetonitrile under a protective gas atmosphere at room temperature. The mixture was boiled under reflux for 2 hours and cooled to room temperature. The resulting precipitate was filtered off with suction and washed with 50 ml of acetonitrile. The residue was stirred with 100 ml of methanol, filtered off with suction, washed with a little methanol and dried at 40° C. under vacuum overnight. 13.7 g (28.9 mmol, 85%) of the required product were obtained. Melting point: about 171–173° C.

We claim:

1. A compound of the formula (I)

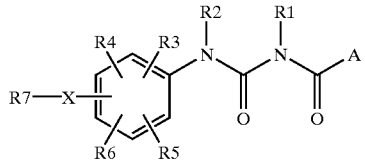

wherein

A is phenyl, or naphthyl, wherein the phenyl or naphthyl radical is optionally substituted up to three times by one or more of the following radicals:

F, Cl, Br, OH, $CF_3$, $NO_2$, CN, $OCF_3$, O—($C_1$–$C_6$)-alkyl, O—($C_1$–$C_6$)-alkenyl, O—($C_1$–$C_6$)-alkynyl, S—($C_1$–$C_6$)-alkyl, S—($C_1$–$C_6$)-alkenyl, S—($C_1$–$C_6$)-alkynyl, SO—($C_1$–$C_6$)-alkyl, $SO_2$—($C_1$–$C_6$)-alkyl, $SO_2$—$NH_2$, ($C_1$–$C_6$)-alkyl, ($C_1$–$C_6$)-alkenyl, ($C_1$–$C_6$)-alkynyl, ($C_3$–$C_7$)-cycloalkyl, ($C_3$–$C_7$)-cycloalkyl-($C_1$–$C_4$)-alkylene, ($C_1$–$C_6$)-alkylene-COOH, ($C_0$–$C_6$)-alkylene-COO($C_1$–$C_7$)-alkyl, $CONH_2$, $CONH(C_1$–$C_6$)-alkyl, CON[($C_1$–$C_6$)-alkyl]$_2$, $CONH(C_3$–$C_6$)-cycloalkyl, ($C_0$–$C_6$)-alkylene-$NH_2$, ($C_0$–$C_6$)-alkylene-NH ($C_2$–$C_6$)-alkyl, ($C_0$–$C_6$)-alkylene-N[($C_1$–$C_6$)-alkyl]$_2$, NH—CO—($C_1$–$C_6$)-Alkyl, NH—CO-phenyl, or NH—$SO_2$-phenyl, wherein the phenyl ring in NH—CO-phenyl, or NH—$SO_2$-phenyl is optionally substituted up to twice by one or two of the following radicals:

F, Cl, CN, OH, ($C_1$–$C_6$)-alkyl, O—($C_1$–$C_6$)-alkyl, $CF_3$, $OCF_3$, COOH, COO($C_1$–$C_6$)-alkyl, or $CONH_2$;

R1, R2 are, independently of one another:
H, $(C_1–C_6)$-alkyl, O—$(C_1–C_6)$-alkyl, CO—$(C_1–C_6)$-alkyl, COO—$(C_1–C_6)$-alkyl, $(C_1–C_6)$-alkylene-COOH, or $(C_1–C_6)$-alkylene-COO—$(C_1–C_6)$-alkyl;

R3, R4, R5, R6 are, independently of one another:
H, F, Cl, Br, OH, $CF_3$, $NO_2$, CN, $OCF_3$, O—$(C_1–C_6)$-alkyl, O—$(C_1–C_6)$-alkenyl, O—$(C_1–C_6)$-alkynyl, S—$(C_1–C_6)$-alkyl, S—$(C_1–C_6)$-alkenyl, S—$(C_1–C_6)$-alkynyl, SO—$(C_1–C_6)$-alkyl, $SO_2$—$(C_1–C_6)$-alkyl, $SO_2$—$NH_2$, $(C_1–C_6)$-alkyl, $(C_1–C_6)$-alkenyl, $(C_1–C_6)$-alkynyl, $(C_3–C_7)$-cycloalkyl, $(C_3–C_7)$-cycloalkyl-$(C_1–C_4)$-alkylene, COOH, COO$(C_1–C_6)$-alkyl, $CONH_2$, CONH$(C_1–C_6)$-alkyl, CON$[(C_1–C_6)$-alkyl$]_2$, CONH$(C_3–C_7)$-cycloalkyl, $NH_2$, NH$(C_1–C_6)$-alkyl, N$[(C_1–C_6)$-alkyl$]_2$, NH—CO—$(C_1–C_6)$-alkyl, NH—CO-phenyl, or NH—$SO_2$-phenyl, wherein the phenyl ring in NH—CO-phenyl, or NH—$SO_2$-phenyl is optionally substituted up to twice by one or two of the following radicals:
F, Cl, CN, OH, $(C_1–C_6)$-Alkyl, O—$(C_1–C_6)$-alkyl, $CF_3$, $OCF_3$, COOH, COO$(C_1–C_6)$-alkyl, or $CONH_2$;

X is O or S;

R7 is $(C_1–C_{10})$-alkylene-COOH, $(C_6–C_{10})$-alkylene-COO—$(C_1–C_6)$-alkyl, $(C_1–C_{10})$-alkylene-$CONH_2$, $(C_1–C_{10})$-alkylene-CONH—$(C_1–C_6)$-alkyl, $(C_1–C_{10})$-alkylene-CON—$[(C_1–C_6)$-alkyl$]_2$, $(C_1–C_{10})$-alkylene-$NH_2$, $(C_4–C_{10})$-alkylene-NH—$(C_1–C_6)$-alkyl, $(C_1–C_{10})$-alkylene-N$[(C_1–C_6)$-alkyl$]_2$, or $(C_1–C_{10})$-alkylene-B;

wherein
B is $(C_3–C_7)$-cycloalkyl, phenyl, pyrrolyl, imidazolyl, thiazolyl, azetidinyl, thienyl, piperidinyl, pyrrolidinyl, morpholinyl, pyridyl-methyl, or furyl, wherein cycloalkyl, phenyl, pyrrolyl, imidazolyl, thiazolyl, azetidinyl, thienylmethyl, piperidinyl, pyrrolidinyl, morpholinyl, pyridyl or furyl may in each case be optionally substituted up to twice by one or two of the following radicals:
Cl, F, CN, $CF_3$, $OCF_3$, COOH, COO—$(C_1–C_6)$-alkyl, $CONH_2$, CONH—$(C_1–C_6)$-alkyl, CON—$[(C_1–C_6)$-alkyl$]_2$, $(C_1–C_6)$-alkyl, OH, or O—$(C_1–C_6)$-alkyl;

or a physiologically tolerated salt thereof,
except the compounds of the formula

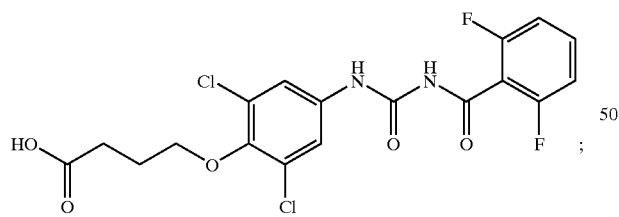

except compounds of the formula (I) in which the radicals are, at the same time:

| | |
|---|---|
| A | phenyl; |
| X | O; |
| R1 | H; |
| R7 | -$(C_1–C_4)$-alkyl-B; |
| B | $(C_3–C_7)$-cycloalkyl, or heteroaryl; and | wherein, in the compounds of the formula (I) when X=O; R1–R2=H; and one of R3–R6 is Cl and the others are hydrogen, the $(C_1–C_{10})$-alkylene-COOH group in R7 is instead a $(C_2–C_{10})$-alkylene-COOH group.

2. The compound of the formula (I) as claimed in claim 1, wherein

A is phenyl, or naphthyl, wherein the phenyl or naphthyl radical are optionally substituted up to three times by one or more of the following radicals:
F, Cl, Br, OH, $CF_3$, $NO_2$, CN, $OCF_3$, O—$(C_1–C_6)$-alkyl, O—$(C_1–C_6)$-alkenyl, O—$(C_1–C_6)$-alkynyl, S—$(C_1–C_6)$-alkyl, S—$(C_1–C_6)$-alkenyl, S—$(C_1–C_6)$-alkynyl, SO—$(C_1–C_6)$-alkyl, $SO_2$—$(C_1–C_6)$-alkyl, $SO_2$—$NH_2$, $(C_1–C_6)$-alkylene, $(C_1–C_6)$-alkenyl, $(C_1–C_6)$-alkynyl, $(C_3–C_7)$-cycloalkyl, $(C_3–C_7)$-cycloalkyl-$(C_1–C_4)$-alkylene, $(C_0–C_6)$-alkylene-COOH, $(C_0–C_6)$-alkylene-COO$(C_1–C_6)$-alkyl, $CONH_2$, CONH$(C_1–C_6)$-alkyl, CON$[(C_1–C_6)$-alkyl$]_2$, CONH$(C_3–C_7)$-cycloalkyl, $(C_0–C_6)$-alkylene-$NH_2$, $(C_0–C_6)$-alkylene-NH$(C_2–C_6)$-alkyl, $(C_0–C_6)$-alkylene-N$[(C_1–C_6)$-alkyl$]_2$, NH—CO—$(C_1–C_6)$-alkyl, NH—CO-phenyl, or NH—$SO_2$-phenyl, wherein the phenyl ring in NH—CO-phenyl, or NH—$SO_2$-phenyl is optionally substituted up to twice by one or two of the following radicals:
F, Cl, CN, OH, $(C_1–C_6)$-alkyl, O—$(C_1–C_6)$-alkyl, $CF_3$, $OCF_3$, COOH, COO$(C_1–C_6)$-alkyl or $CONH_2$;

R1, R2 are, independently of one another,
H, $(C_1–C_6)$-alkyl, O—$(C_1–C_6)$-alkyl, CO—$(C_1–C_6)$-alkyl, COO—$(C_1–C_6)$-alkyl, $(C_1–C_6)$-alkylene-COOH, or $(C_1–C_6)$-alkylene-COO—$(C_1–C_6)$-alkyl;

R3, R4, R5, R6 are, independently of one another,
H, F, Cl, Br, OH, $CF_3$, $NO_2$, CN, $OCF_3$, O—$(C_1–C_6)$-alkyl, O—$(C_1–C_6)$-alkenyl, O—$(C_1–C_6)$-alkynyl, S—$(C_1–C_6)$-alkyl, S—$(C_1–C_6)$-alkenyl, S—$(C_1–C_6)$-alkynyl, SO—$(C_1–C_6)$-alkyl, $SO_2$—$(C_1–C_6)$-alkyl, $SO_2$—$NH_2$, $(C_1–C_6)$-alkyl, $(C_1–C_6)$-alkenyl, $(C_1–C_6)$-alkynyl, $(C_3–C_7)$-cycloalkyl, $(C_3–C_7)$-cycloalkyl-$(C_1–C_4)$-alkylene, COOH, COO$(C_1–C_6)$-alkyl, $CONH_2$, CONH$(C_1–C_6)$-alkyl, CON$[(C_1–C_6)$-alkyl$]_2$, CONH$(C_3–C_7)$-cycloalkyl, $NH_2$, NH$(C_1–C_6)$-alkyl, N$[(C_1–C_6)$-alkyl$]_2$, NH—CO—$(C_1–C_6)$-alkyl, NH—CO-phenyl, or NH—$SO_2$-phenyl, wherein the phenyl ring in NH—CO-phenyl, or NH—$SO_2$-phenyl is optionally substituted up to twice by one or two of the following radicals:
F, Cl, CN, OH, $(C_1–C_6)$-alkyl, O—$(C_1–C_6)$-alkyl, $CF_3$, $OCF_3$, COOH, COO$(C_1–C_6)$-alkyl or $CONH_2$;

X is O or S;

R7 is $(C_1–C_{10})$-alkylene-COOH, $(C_6–C_{10})$-alkylene-COO—$(C_1–C_6)$-alkyl, $(C_1–C_{10})$-alkylene-$CONH_2$, $(C_1–C_{10})$-alkylene-CONH—$(C_1–C_6)$-alkyl, $(C_1–C_{10})$-alkylene-CON—$[(C_1–C_6)$-alkyl$]_2$, $(C_1–C_{10})$-alkylene-$NH_2$, $(C_4–C_{10})$-alkylene-NH—$(C_1–C_6)$-alkyl, $(C_1–C_{10})$-alkylene-N$[(C_1–C_6)$-alkyl$]_2$, or $(C_1–C_{10})$-alkylene-B;

wherein
B is $(C_3–C_7)$-cycloalkyl, phenyl, pyrrolyl, imidazolyl, thiazolyl, azetidinyl, thienyl-methyl, piperidinyl, pyrrolidinyl, morpholinyl, pyridyl-methyl or furyl, wherein cycloalkyl, phenyl, pyrrolyl, imidazolyl, thiazolyl, azetidinyl, thienyl, piperidinyl, pyrrolidinyl, morpholinyl, pyridyl or furyl may in each case be optionally substituted up to twice by one or two of the following radicals:

Cl, F, CN, CF3, OCF3, COOH, COO—$(C_1-C_6)$-alkyl, CONH2, CONH—$(C_1-C_6)$-alkyl, CON—$[(C1-C6)-alkyl]2$, $(C_1-C_6)$-alkyl, OH, or O—$(C_1-C_6)$-alkyl;
or a physiologically tolerated salt thereof,
except the compounds of the formula

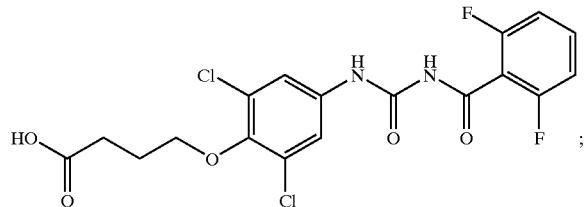

except the compounds of the formula (I) in which the radicals are, at the same time:

| | |
|---|---|
| A | phenyl; |
| X | O; |
| R1 | H; |
| R7 | -$(C_1-C_4)$-alkyl-B; |
| B | $(C_3-C_7)$-cycloalkyl, or heteroaryl; and | wherein, in the compounds of the formula (I) when X=O; R1–R2=H; and one of R3–R6 is Cl and the others are hydrogen, the $(C_1-C_{10})$-alkylene-COOH group in R7 is instead a $(C_2-C_{10})$-alkylene-COOH group.

3. The compound of the formula (I) as claimed in claim 1, wherein
A is phenyl,
wherein the phenyl radical is optionally substituted up to twice by one or two of the following radicals:
F, Cl, Br, O—$(C_1-C_6)$-alkyl;
R1, R2 are, independently of one another, H, $(C_1-C_6)$-alkyl, or CO—$(C_1-C_6)$-alkyl;
R3, R4, R5, R6 are, independently of one another, H, Cl, F, $(C_1-C_6)$-alkyl, O—$(C_1-C_6)$-alkyl, —COO—$(C_1-C_6)$-alkyl;
X is O;
R7 is $(C_1-C_{10})$-alkylene-COOH, $(C_6-C_{10})$-alkylene-COO—$(C_1-C_6)$-alkyl, or $(C_1-C_{10})$-alkylene-CONH_2;
or a physiologically tolerated salt thereof,
except the compounds of the formula

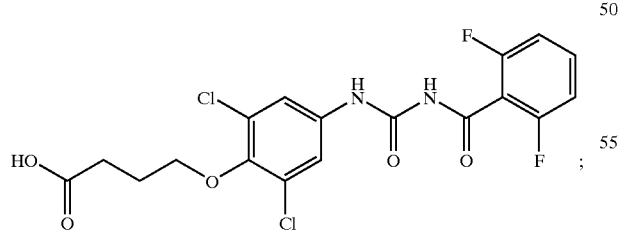

and
wherein, in the compounds of the formula (I) when X=O; R1–R2=H; and one of R3–R6 is Cl and the others are hydrogen, the $(C_1-C_{10})$-alkylene-COOH group in R7 is instead a $(C_2-C_{10})$-alkylene-COOH group.

4. A pharmaceutical composition comprising one or more of the compounds of the formula (I)

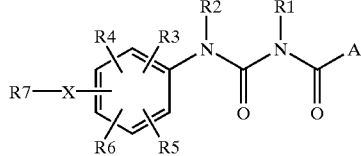

wherein
A is phenyl, or naphthyl,
wherein the phenyl or naphthyl radical is optionally substituted up to three times by one or more of the following radicals:
F, Cl, Br, OH, CF_3, NO_2, CN, OCF_3, O—$(C_1-C_6)$-alkyl, O—$(C_1-C_6)$-alkenyl, O—$(C_1-C_6)$-alkynyl, S—$(C_1-C_6)$-alkyl, S—$(C_1-C_6)$-alkenyl, S—$(C_1-C_6)$-alkynyl, SO—$(C_1-C_6)$-alkyl, SO_2—$(C_1-C_6)$-alkyl, SO_2—NH_2, $(C_1-C_6)$-alkyl, $(C_1-C_6)$-alkenyl, $(C_1-C_6)$-alkynyl, $(C_3-C_7)$-cycloalkyl, $(C_3-C_7)$-cycloalkyl-$(C_1-C_4)$-alkylene, $(C_0-C_6)$-alkylene-COOH, $(C_0-C_6)$-alkylene-COO$(C_1-C_7)$-alkyl, CONH_2, CONH$(C_1-C_6)$-alkyl, CON$[(C_1-C_6)$-alkyl$]_2$, CONH$(C_3-C_6)$-cycloalkyl, (CO—$C_6)$-alkylene-NH_2, $(C_0-C_6)$-alkylene-NH$(C_2-C_6)$-alkyl, $(C_0-C_6)$-alkylene-N$[(C_1-C_6)$-alkyl$]_2$, NH—CO—$(C_1-C_6)$-Alkyl, NH—CO-phenyl, or NH—SO_2-phenyl, wherein the phenyl ring in NH—CO-phenyl, or NH—SO_2-phenyl is optionally substituted up to twice by one or two of the following radicals:
F, Cl, CN, OH, $(C_1-C_6)$-alkyl, O—$(C_1-C_6)$-alkyl, CF_3, OCF_3, COOH, COO$(C_1-C_6)$-alkyl, or CONH_2;
R1, R2 are, independently of one another:
H, $(C_1-C_6)$-alkyl, O—$(C_1-C_6)$-alkyl, CO—$(C_1-C_6)$-alkyl, COO—$(C_1-C_6)$-alkyl, $(C_1-C_6)$-alkylene-COOH, or $(C_1-C_6)$-alkylene-COO—$(C_1-C_6)$-alkyl;
R3, R4, R5, R6 are, independently of one another:
H, F, Cl, Br, OH, CF_3, NO_2, CN, OCF_3, O—$(C_1-C_6)$-alkyl, O—$(C_1-C_6)$-alkenyl, O—$(C_1-C_6)$-alkynyl, S—$(C_1-C_6)$-alkyl, S—$(C_1-C_6)$-alkenyl, S—$(C_1-C_6)$-alkynyl, SO—$(C_1-C_6)$-alkyl, SO_2—$(C_1-C_6)$-alkyl, SO_2—NH_2, $(C_1-C_6)$-alkyl, $(C_1-C_6)$-alkenyl, $(C_1-C_6)$-alkynyl, $(C_3-C_7)$-cycloalkyl, $(C_3-C_7)$-cycloalkyl-$(C_1-C_4)$-alkylene, COOH, COO $(C_1-C_6)$-alkyl, CONH_2, CONH$(C_1-C_6)$-alkyl, CON $[(C_1-C_6)$-alkyl$]2$, CONH$(C_3-C_7)$-cycloalkyl, NH_2, NH$(C_1-C_6)$-alkyl, N$[(C_1-C_6)$-alkyl$]_2$, NH—CO—$(C_1-C_6)$-alkyl, NH—CO-phenyl, or NH—SO_2-phenyl, wherein the phenyl ring in NH—CO-phenyl, or NH—SO_2-phenyl is optionally substituted up to twice by one or two of the following radicals:
F, Cl, CN, OH, $(C_1-C_6)$-Alkyl, O—$(C_1-C_6)$-alkyl, CF_3, OCF_3, COOH, COO$(C_1-C_6)$-alkyl, or CONH_2;
X is O or S;
R7 is $(C_1-C_{10})$-alkylene-COOH, $(C_6-C_{10})$-alkylene-COO—$(C_1-C_6)$-alkyl, $(C_1-C_{10})$-alkylene-CONH_2, $(C_1-C_{10})$-alkylene-CONH—$(C_1-C_6)$-alkyl, $(C_1-C_{10})$-alkylene-CON—$[(C_1-C_6)$-alkyl$]_2$, $(C_1-C_{10})$-alkylene-NH_2, $(C_1-C_{10})$-alkylene-NH—$(C_1-C_6)$-alkyl, $(C_1-C_{10})$-alkylene-N$[(C_1-C_6)$-alkyl$]_2$, or $(C_1-C_{10})$-alkylene-B;
wherein
B is $(C_3-C_7)$-cycloalkyl, phenyl, pyrrolyl, imidazolyl, thiazolyl, azetidinyl, thienyl, piperidinyl, pyrrolidinyl, morpholinyl, pyridyl-methyl, or furyl, wherein cycloalkyl, phenyl, pyrrolyl, imidazolyl, thiazolyl, azetidinyl, thienylmethyl, piperidinyl, pyrrolidinyl, morpholinyl, pyridyl or furyl may in each case be optionally substituted up to twice by one or two of the following radicals:

Cl, F, CN, $CF_3$, $OCF_3$, COOH, COO—$(C_1$–$C_6)$-alkyl, $CONH_2$, CONH—$(C_1$–$C_6)$-alkyl, CON—$[(C_1$–$C_6)$-alkyl]$_2$, $(C_1$–$C_6)$-alkyl, OH, or O—$(C_1$–$C_6)$-alkyl;

or a physiologically tolerated salt thereof, except the compounds of the formula

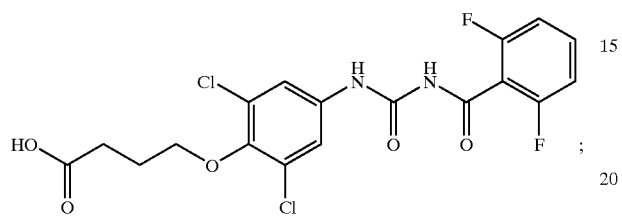

except compounds of the formula (I) in which the radicals are, at the same time:

| | |
|---|---|
| A | phenyl; |
| X | O; |
| R1 | H; |
| R7 | -$(C_1$–$C_4)$-alkyl-B; |
| B | $(C_3$–$C_7)$-cycloalkyl, or heteroaryl; | and a pharmaceutically acceptable carrier.

5. A pharmaceutical composition comprising one or more of the compounds of the formula (I)

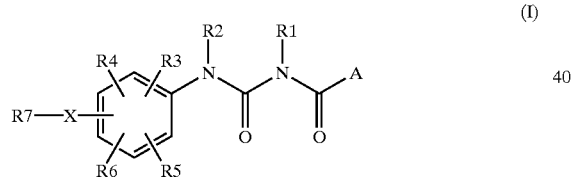

(I)

wherein

A is phenyl, or naphthyl,
wherein the phenyl or naphthyl radical is optionally substituted up to three times by one or more of the following radicals:
F, Cl, Br, OH, $CF_3$, $NO_2$, CN, $OCF_3$, O—$(C_1$–$C_6)$-alkyl, O—$(C_1$–$C_6)$-alkenyl, O—$(C_1$–$C_6)$-alkynyl, S—$(C_1$–$C_6)$-alkyl, S—$(C_1$–$C_6)$-alkenyl, S—$(C_1$–$C_6)$-alkynyl, SO—$(C_1$–$C_6)$-alkyl, $SO_2$—$(C_1$–$C_6)$-alkyl, $SO_2$—$NH_2$, $(C_1$–$C_6)$-alkyl, $(C_1$–$C_6)$-alkenyl, $(C_1$–$C_6)$-alkynyl, $(C_3$–$C_7)$-cycloalkyl, $(C_3$–$C_7)$-cycloalkyl-$(C_1$–$C_4)$-alkylene, $(C_0$–$C_6)$-alkylene-COOH, $(C_0$–$C_6)$-alkylene-COO$(C_1$–$C_7)$-alkyl, $CONH_2$, CONH$(C_1$–$C_6)$-alkyl, CON$[(C_1$–$C_6)$-alkyl]$_2$, CONH$(C_3$–$C_6)$-cycloalkyl, $(C_0$–$C_6)$-alkylene-$NH_2$, $(C_0$–$C_6)$-alkylene-NH$(C_2$–$C_6)$-alkyl, $(C_0$–$C_6)$-alkylene-N$[(C_1$–$C_6)$-alkyl]$_2$, NH—CO—$(C_1$–$C_6)$-Alkyl, NH—CO-phenyl, or NH—$SO_2$-phenyl, wherein the phenyl ring in NH—CO-phenyl, or NH—$SO_2$-phenyl is optionally substituted up to twice by one or two of the following radicals:

F, Cl, CN, OH, $(C_1$–$C_6)$-alkyl, O—$(C_1$–$C_6)$-alkyl, $CF_3$, $OCF_3$, COOH, COO$(C_1$–$C_6)$-alkyl, or $CONH_2$;

R1, R2 are, independently of one another:
H, $(C_1$–$C_6)$-alkyl, O—$(C_1$–$C_6)$-alkyl, CO—$(C_1$–$C_6)$-alkyl, COO—$(C_1$–$C_6)$-alkyl, $(C_1$–$C_6)$-alkylene-COOH, or $(C_1$–$C_6)$-alkylene-COO—$(C_1$–$C_6)$-alkyl;

R3, R4, R5, R6 are, independently of one another:
H, F, Cl, Br, OH, $CF_3$, $NO_2$, CN, $OCF_3$, O—$(C_1$–$C_6)$-alkyl, O—$(C_1$–$C_6)$-alkenyl, O—$(C_1$–$C_6)$-alkynyl, S—$(C_1$–$C_6)$-alkyl, S—$(C_1$–$C_6)$-alkenyl, S—$(C_1$–$C_6)$-alkynyl, SO—$(C_1$–$C_6)$-alkyl, $SO_2$—$(C_1$–$C_6)$-alkyl, $SO_2$—$NH_2$, $(C_1$–$C_6)$-alkyl, $(C_1$–$C_6)$-alkenyl, $(C_1$–$C_6)$-alkynyl, $(C_3$–$C_7)$-cycloalkyl, $(C_3$–$C_7)$-cycloalkyl-$(C_1$–$C_4)$-alkylene, COOH, COO $(C_1$–$C_6)$-alkyl, $CONH_2$, CONH$(C_1$–$C_6)$-alkyl, CON $[(C_1$–$C_6)$-alkyl]$_2$, CONH$(C_3$–$C_7)$-cycloalkyl, $NH_2$, NH$(C_1$–$C_6)$-alkyl, N$[(C_1$–$C_6)$-alkyl]$_2$, NH—CO—$(C_1$–$C_6)$-alkyl, NH—CO-phenyl, or NH—$SO_2$-phenyl, wherein the phenyl ring in NH—CO-phenyl, or NH—$SO_2$-phenyl is optionally substituted up to twice by one or two of the following radicals:

F, Cl, CN, OH, $(C_1$–$C_6)$-Alkyl, O—$(C_1$–$C_6)$-alkyl, $CF_3$, $OCF_3$, COOH, COO$(C_1$–$C_6)$-alkyl, or $CONH_2$;

X is O or S;

R7 is $(C_1$–$C_{10})$-alkylene-COOH, $(C_6$–$C_{10})$-alkylene-COO—$(C_1$–$C_6)$-alkyl, $(C_1$–$C_{10})$-alkylene-$CONH_2$, $(C_1$–$C_{10})$-alkylene-CONH—$(C_1$–$C_6)$-alkyl, $(C_1$–$C_{10})$-alkylene-CON—$[(C_1$–$C_6)$-alkyl]$_2$, $(C_1$–$C_{10})$-alkylene-$NH_2$, $(C_1$–$C_{10})$-alkylene-NH—$(C_1$–$C_6)$-alkyl, $(C_1$–$C_{10})$-alkylene-N$[(C_1$–$C_6)$-alkyl]$_2$, or $(C_1$–$C_{10})$-alkylene-B;

wherein

B is $(C_3$–$C_7)$-cycloalkyl, phenyl, pyrrolyl, imidazolyl, thiazolyl, azetidinyl, thienyl, piperidinyl, pyrrolidinyl, morpholinyl, pyridyl-methyl, or furyl, wherein cycloalkyl, phenyl, pyrrolyl, imidazolyl, thiazolyl, azetidinyl, thienylmethyl, piperidinyl, pyrrolidinyl, morpholinyl, pyridyl or furyl may in each case be optionally substituted up to twice by one or two of the following radicals:

Cl, F, CN, $CF_3$, $OCF_3$, COOH, COO—$(C_1$–$C_6)$-alkyl, $CONH_2$, CONH—$(C_1$–$C_6)$-alkyl, CON—$[(C_1$–$C_6)$-alkyl]$_2$, $(C_1$–$C_6)$-alkyl, OH, or O—$(C_1$–$C_6)$-alkyl;

or a physiologically tolerated salt thereof, except the compounds of the formula

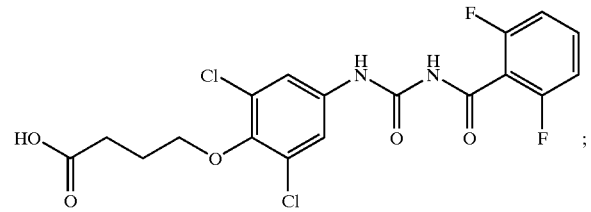

and except compounds of the formula (I) in which the radicals are, at the same time:

| | |
|---|---|
| A | phenyl; |
| X | O; |
| R1 | H; |
| R7 | -(C$_1$-C$_4$)-alkyl-B; |
| B | (C$_3$-C$_7$)-cycloalkyl, or heteroaryl; | and one or more blood glucose-lowering active ingredients.

6. A method for lowering blood glucose, comprising administering to a patient in need thereof an effective amount of at least one compound of the formula (I)

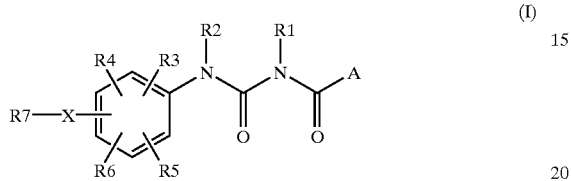
(I)

wherein
A is phenyl, or naphthyl,
wherein the phenyl or naphthyl radical is optionally substituted up to three times by one or more of the following radicals:
F, Cl, Br, OH, CF$_3$, NO$_2$, CN, OCF$_3$, O—(C$_1$-C$_6$)-alkyl, O—(C$_1$-C$_6$)-alkenyl, O—(C$_1$-C$_6$)-alkynyl, S—(C$_1$-C$_6$)-alkyl, S—(C$_1$-C$_6$)-alkenyl, S—(C$_1$-C$_6$)-alkynyl, SO—(C$_1$-C$_6$)-alkyl, SO$_2$—(C$_1$-C$_6$)-alkyl, SO$_2$—NH$_2$, (C$_1$-C$_6$)-alkyl, (C$_1$-C$_6$)-alkenyl, (C$_1$-C$_6$)-alkynyl, (C$_3$-C$_7$)-cycloalkyl, (C$_3$-C$_7$)-cycloalkyl-(C$_1$-C$_4$)-alkylene, (C$_0$-C$_6$)-alkylene-COOH, (C$_0$-C$_6$)-alkylene-COO(C$_1$-C$_7$)-alkyl, CONH$_2$, CONH(C$_1$-C$_6$)-alkyl, CON[(C$_1$-C$_6$)-alkyl]$_2$, CONH(C$_3$-C$_6$)-cycloalkyl, (C$_0$-C$_6$)-alkylene-NH$_2$, (C$_0$-C$_6$)-alkylene-NH(C$_2$-C$_6$)-alkyl, (C$_0$-C$_6$)-alkylene-N[(C$_1$-C$_6$)-alkyl]$_2$, NH—CO—(C$_1$-C$_6$)-Alkyl, NH—CO-phenyl, or NH—SO$_2$-phenyl, wherein the phenyl ring in NH—CO-phenyl, or NH—SO$_2$-phenyl is optionally substituted up to twice by one or two of the following radicals:
F, Cl, CN, OH, (C$_1$-C$_6$)-alkyl, O—(C$_1$-C$_6$)-alkyl, CF$_3$, OCF$_3$, COOH, COO(C$_1$-C$_6$)-alkyl, or CONH$_2$;
R1, R2 are, independently of one another:
H, (C$_1$-C$_6$)-alkyl, O—(C$_1$-C$_6$)-alkyl, CO—(C$_1$-C$_6$)-alkyl, COO—(C$_1$-C$_6$)-alkyl, (C$_1$-C$_6$)-alkylene-COOH, or (C$_1$-C$_6$)-alkylene-COO—(C$_1$-C$_6$)-alkyl;
R3, R4, R5, R6 are, independently of one another:
H, F, Cl, Br, OH, CF$_3$, NO$_2$, CN, OCF$_3$, O—(C$_1$-C$_6$)-alkyl, O—(C$_1$-C$_6$)-alkenyl, O—(C$_1$-C$_6$)-alkynyl, S—(C$_1$-C$_6$)-alkyl, S—(C$_1$-C$_6$)-alkenyl, S—(C$_1$-C$_6$)-alkynyl, SO—(C$_1$-C$_6$)-alkyl, SO$_2$—(C$_1$-C$_6$)-alkyl, SO$_2$—NH$_2$, (C$_1$-C$_6$)-alkyl, (C$_1$-C$_6$)-alkenyl, (C$_1$-C$_6$)-alkynyl, (C$_3$-C$_7$)-cycloalkyl, (C$_3$-C$_7$)-cycloalkyl-(C$_1$-C$_4$)-alkylene, COOH, COO(C$_1$-C$_6$)-alkyl, CONH$_2$, CONH(C$_1$-C$_6$)-alkyl, CON[(C$_1$-C$_6$)-alkyl]$_2$, CONH(C$_3$-C$_7$)-cycloalkyl, NH$_2$, NH(C$_1$-C$_6$)-alkyl, N[(C$_1$-C$_6$)-alkyl]$_2$, NH—CO—(C$_1$-C$_6$)-alkyl, NH—CO-phenyl, or NH—SO$_2$-phenyl, wherein the phenyl ring in NH—CO-phenyl, or NH—SO$_2$-phenyl is optionally substituted up to twice by one or two of the following radicals:
F, Cl, CN, OH, (C$_1$-C$_6$)-Alkyl, O—(C$_1$-C$_6$)-alkyl, CF$_3$, OCF$_3$, COOH, COO(C$_1$-C$_6$)-alkyl, or CONH$_2$;

X is O or S;
R7 is (C$_1$-C$_{10}$)-alkylene-COOH, (C$_6$-C$_{10}$)-alkylene-COO—(C$_1$-C$_6$)-alkyl, (C$_1$-C$_{10}$)-alkylene-CONH$_2$, (C$_1$-C$_{10}$)-alkylene-CONH—(C$_1$-C$_6$)-alkyl, (C$_1$-C$_{10}$)-alkylene-CON—[(C$_1$-C$_6$)-alkyl]$_2$, (C$_1$-C$_{10}$)-alkylene-NH$_2$, (C$_1$-C$_{10}$)-alkylene-NH—(C$_1$-C$_6$)-alkyl, (C$_1$-C$_{10}$)-alkylene-N[(C$_1$-C$_6$)-alkyl]$_2$, or (C$_1$-C$_{10}$)-alkylene-B;
wherein
B is (C$_3$-C$_7$)-cycloalkyl, phenyl, pyrrolyl, imidazolyl, thiazolyl, azetidinyl, thienyl, piperidinyl, pyrrolidinyl, morpholinyl, pyridyl-methyl, or furyl, wherein cycloalkyl, phenyl, pyrrolyl, imidazolyl, thiazolyl, azetidinyl, thienylmethyl, piperidinyl, pyrrolidinyl, morpholinyl, pyridyl or furyl may in each case be optionally substituted up to twice by one or two of the following radicals:
Cl, F, CN, CF$_3$, OCF$_3$, COOH, COO—(C$_1$-C$_6$)-alkyl, CONH$_2$, CONH—(C$_1$-C$_6$)-alkyl, CON—[(C$_1$-C$_6$)-alkyl]$_2$, (C$_1$-C$_6$)-alkyl, OH, or O—(C$_1$-C$_6$)-alkyl;
or a physiologically tolerated salt thereof,
except the compounds of the formula

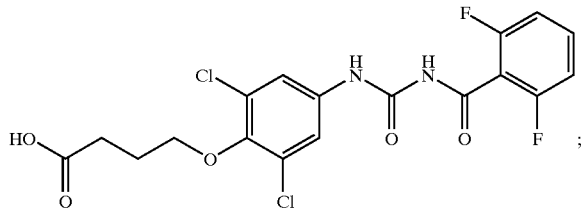

and
except compounds of the formula (I) in which the radicals are, at the same time:

| | |
|---|---|
| A | phenyl; |
| X | O; |
| R1 | H; |
| R7 | -(C$_1$-C$_4$)-alkyl-B; |
| B | (C$_3$-C$_7$)-cycloalkyl, or heteroaryl. |

7. The method according to claim 6, further comprising administering at least one other blood glucose-lowering active ingredient.

8. A method for treating type II diabetes, comprising administering to a patient in need thereof an effective amount of at least one compound of the formula (I)

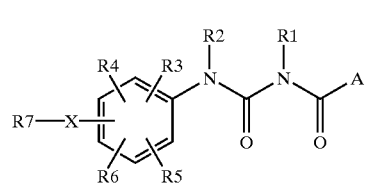
(I)

wherein
A is phenyl, or naphthyl,
wherein the phenyl or naphthyl radical is optionally substituted up to three times by one or more of the following radicals:
F, Cl, Br, OH, CF$_3$, NO$_2$, CN, OCF$_3$, O—(C$_1$-C$_6$)-alkyl, O—(C$_1$-C$_6$)-alkenyl, O—(C$_1$-C$_6$)-alkynyl, S—($C_1$–$C_6$)-alkyl, S—($C_1$–$C_6$)-alkenyl, S—($C_1$–$C_6$)-alkynyl, SO—($C_1$–$C_6$)-alkyl, $SO_2$—($C_1$–$C_6$)-alkyl, $SO_2$—$NH_2$, ($C_1$–$C_6$)-alkyl, ($C_1$–$C_6$)-alkenyl, ($C_1$–$C_6$)-alkynyl, ($C_3$–$C_7$)-cycloalkyl, ($C_3$–$C_7$)-cycloalkyl-($C_1$–$C_4$)-alkylene, ($C_0$–$C_6$)-alkylene-COOH, ($C_0$–$C_6$)-alkylene-COO($C_1$–$C_7$)-alkyl, $CONH_2$, CONH($C_1$–$C_6$)-alkyl, CON[($C_1$–$C_6$)-alkyl]$_2$, CONH($C_3$–$C_6$)-cycloalkyl, ($C_0$–$C_6$)-alkylene-$NH_2$, ($C_0$–$C_6$)-alkylene-NH($C_2$–$C_6$)-alkyl, ($C_0$–$C_6$)-alkylene-N[($C_1$–$C_6$)-alkyl]$_2$, NH—CO—($C_1$–$C_6$)-Alkyl, NH—CO-phenyl, or NH—$SO_2$-phenyl, wherein the phenyl ring in NH—CO-phenyl, or NH—$SO_2$-phenyl is optionally substituted up to twice by one or two of the following radicals:

F, Cl, CN, OH, ($C_1$–$C_6$)-alkyl, O—($C_1$–$C_6$)-alkyl, $CF_3$, $OCF_3$, COOH, COO($C_1$–$C_6$)-alkyl, or $CONH_2$;

R1, R2 are, independently of one another:

H, ($C_1$–$C_6$)-alkyl, O—($C_1$–$C_6$)-alkyl, CO—($C_1$–$C_6$)-alkyl, COO—($C_1$–$C_6$)-alkyl, ($C_1$–$C_6$)-alkylene-COOH, or ($C_1$–$C_6$)-alkylene-COO—($C_1$–$C_6$)-alkyl;

R3, R4, R5, R6 are, independently of one another:

H, F, Cl, Br, OH, $CF_3$, $NO_2$, CN, $OCF_3$, O—($C_1$–$C_6$)-alkyl, O—($C_1$–$C_6$)-alkenyl, O—($C_1$–$C_6$)-alkynyl, S—($C_1$–$C_6$)-alkyl, S—($C_1$–$C_6$)-alkenyl, S—($C_1$–$C_6$)-alkynyl, SO—($C_1$–$C_6$)-alkyl, $SO_2$—($C_1$–$C_6$)-alkyl, $SO_2$—$NH_2$, ($C_1$–$C_6$)-alkyl, ($C_1$–$C_6$)-alkenyl, ($C_1$–$C_6$)-alkynyl, ($C_3$–$C_7$)-cycloalkyl, ($C_3$–$C_7$)-cycloalkyl-($C_1$–$C_4$)-alkylene, COOH, COO($C_1$–$C_6$)-alkyl, $CONH_2$, CONH($C_1$–$C_6$)-alkyl, CON[($C_1$–$C_6$)-alkyl]$_2$, CONH($C_3$–$C_7$)-cycloalkyl, $NH_2$, NH($C_1$–$C_6$)-alkyl, N[($C_1$–$C_6$)-alkyl]$_2$, NH—CO—($C_1$–$C_6$)-alkyl, NH—CO-phenyl, or NH—$SO_2$-phenyl, wherein the phenyl ring in NH—CO-phenyl, or NH—$SO_2$-phenyl is optionally substituted up to twice by one or two of the following radicals:

F, Cl, CN, OH, ($C_1$–$C_6$)-Alkyl, O—($C_1$–$C_6$)-alkyl, $CF_3$, $OCF_3$, COOH, COO($C_1$–$C_6$)-alkyl, or $CONH_2$;

X is O or S;

R7 is ($C_1$–$C_{10}$)-alkylene-COOH, ($C_6$–$C_{10}$)-alkylene-COO—($C_1$–$C_6$)-alkyl, ($C_1$–$C_{10}$)-alkylene-$CONH_2$, ($C_1C_{10}$)-alkylene-CONH—($C_1$–$C_6$)-alkyl, ($C_1$–$C_{10}$)-alkylene-CON—[($C_1$–$C_6$)-alkyl]$_2$, ($C_1$–$C_{10}$)-alkylene-$NH_2$, ($C_1$–$C_{10}$)-alkylene-NH—($C_1$–$C_6$)-alkyl, ($C_1$–$C_{10}$)-alkylene-N[($C_1$–$C_6$)-alkyl]$_2$, or ($C_1$–$C_{10}$)-alkylene-B;

wherein

B is ($C_3$–$C_7$)-cycloalkyl, phenyl, pyrrolyl, imidazolyl, thiazolyl, azetidinyl, thienyl, piperidinyl, pyrrolidinyl, morpholinyl, pyridyl-methyl, or furyl, wherein cycloalkyl, phenyl, pyrrolyl, imidazolyl, thiazolyl, azetidinyl, thienylmethyl, piperidinyl, pyrrolidinyl, morpholinyl, pyridyl or furyl may in each case be optionally substituted up to twice by one or two of the following radicals:

Cl, F, CN, $CF_3$, $OCF_3$, COOH, COO—($C_1$–$C_6$)-alkyl, $CONH_2$, CONH—($C_1$–$C_6$)-alkyl, CON—[($C_1$–$C_6$)-alkyl]$_2$, ($C_1$–$C_6$)-alkyl, OH, or O—($C_1$–$C_6$)-alkyl;

or a physiologically tolerated salt thereof,
except the compounds of the formula

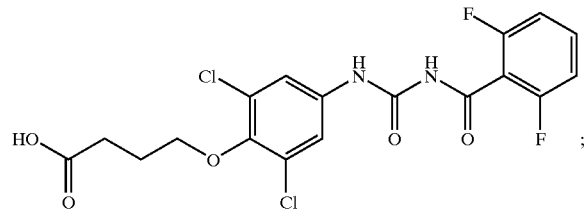

and
except compounds of the formula (I) in which the radicals are, at the same time:

| | |
|---|---|
| A | phenyl; |
| X | O; |
| R1 | H; |
| R7 | -($C_1$–$C_4$)-alkyl-B; |
| B | ($C_3$–$C_7$)-cycloalkyl, or heteroaryl. |

9. A process for producing a pharmaceutical composition, comprising mixing one or more of the compounds of claim 1 with a pharmaceutically acceptable carrier, and converting this mixture into a form suitable for administration.

10. A method for lowering blood glucose, comprising administering to a patient in need thereof an effective amount of at least one compound of the formula (I):

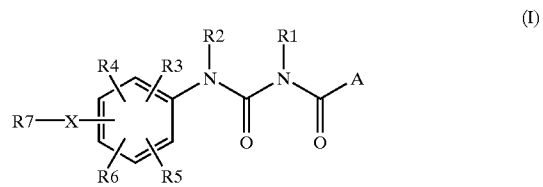

(I)

or a physiologically tolerated salt thereof,
wherein

A is phenyl, or naphthyl, wherein the phenyl or naphthyl radical is optionally substituted up to three times by one or more of the following radicals:

F, Cl, Br, OH, $CF_3$, $NO_2$, CN, $OCF_3$, O—($C_1$–$C_6$)-alkyl, O—($C_1$–$C_6$)-alkenyl, O—($C_1$–$C_6$)-alkynyl, S—($C_1$–$C_6$)-alkyl, S—($C_1$–$C_6$)-alkenyl, S—($C_1$–$C_6$)-alkynyl, SO—($C_1$–$C_6$)-alkyl, $SO_2$—($C_1$–$C_6$)-alkyl, $SO_2$—$NH_2$, ($C_1$–$C_6$)-alkyl, ($C_1$–$C_6$)-alkenyl, ($C_1$–$C_6$)-alkynyl, ($C_3$–$C_7$)-cycloalkyl, ($C_3$–$C_7$)-cycloalkyl-($C_1$–$C_4$)-alkylene, ($C_0$–$C_6$)-alkylene-COOH, ($C_0$–$C_6$)-alkylene-COO($C_1$–$C_7$)-alkyl, $CONH_2$, CONH($C_1$–$C_6$)-alkyl, CON[($C_1$–$C_6$)-alkyl]$_2$, CONH($C_3$–$C_6$)-cycloalkyl, (CO—$C_6$)-alkylene-$NH_2$, ($C_0$–$C_6$)-alkylene-NH($C_2$–$C_6$)-alkyl, ($C_0$–$C_6$)-alkylene-N[($C_1$–$C_6$)-alkyl]$_2$, NH—CO—($C_1$–$C_6$)-Alkyl, NH—CO-phenyl, or NH—$SO_2$-phenyl, wherein the phenyl ring in NH—CO-phenyl, or NH—$SO_2$-phenyl is optionally substituted up to twice by one or two of the following radicals:

F, Cl, CN, OH, ($C_1$–$C_6$)-alkyl, O—($C_1$–$C_6$)-alkyl, $CF_3$, $OCF_3$, COOH, COO($C_1$–$C_6$)-alkyl, or $CONH_2$;

R1, R2 are, independently of one another:
  H, $(C_1-C_6)$-alkyl, O—$(C_1-C_6)$-alkyl, CO—$(C_1-C_6)$-alkyl, COO—$(C_1-C_6)$-alkyl, $(C_1-C_6)$-alkylene-COOH, or $(C_1-C_6)$-alkylene-COO—$(C_1-C_6)$-alkyl;

R3, R4, R5, R6 are, independently of one another:
  H, F, Cl, Br, OH, $CF_3$, $NO_2$, CN, $OCF_3$, O—$(C_1-C_6)$-alkyl, O—$(C_1-C_6)$-alkenyl, O—$(C_1-C_6)$-alkynyl, S—$(C_1-C_6)$-alkyl, S—$(C_1-C_6)$-alkenyl, S—$(C_1-C_6)$-alkynyl, SO—$(C_1-C_6)$-alkyl, $SO_2$—$(C_1-C_6)$-alkyl, $SO_2$—$NH_2$, $(C_1-C_6)$-alkyl, $(C_1-C_6)$-alkenyl, $(C_1-C_6)$-alkynyl, $(C_3-C_7)$-cycloalkyl, $(C_3-C_7)$-cycloalkyl-$(C_1-C_4)$-alkylene, COOH, COO$(C_1-C_6)$-alkyl, $CONH_2$, CONH$(C_1-C_6)$-alkyl, CON[$(C_1-C_6)$-alkyl]$_2$, CONH$(C_3-C_7)$-cycloalkyl, $NH_2$, NH$(C_1-C_6)$-alkyl, N[$(C_1-C_6)$-alkyl]2, NH—CO—$(C_1-C_6)$-alkyl, NH—CO-phenyl, or NH—$SO_2$-phenyl, wherein the phenyl ring in NH—CO-phenyl, or NH—$SO_2$-phenyl is optionally substituted up to twice by one or two of the following radicals:
    F, Cl, CN, OH, $(C_1-C_6)$-Alkyl, O—$(C_1-C_6)$-alkyl, $CF_3$, $OCF_3$, COOH, COO$(C_1-C_6)$-alkyl, or $CONH_2$;

X is O or S;

R7 is $(C_1-C_{10})$-alkylene-COOH, $(C_1-C_{10})$-alkylene-COO—$(C_1-C_6)$-alkyl, $(C_1-C_{10})$-alkylene-$CONH_2$, $(C_1-C_{10})$-alkylene-CONH—$(C_1-C_6)$-alkyl, $(C_1-C_{10})$-alkylene-CON—[$(C_1-C_6)$-alkyl]$_2$, $(C_1-C_{10})$-alkylene-$NH_2$, $(C_1-C_{10})$-alkylene-NH$(C_1-C_6)$-alkyl, $(C_1-C_{10})$-alkylene-N[$(C_1-C_6)$-alkyl]$_2$, or $(C_1-C_{10})$-alkylene-B;
  wherein
  B is $(C_3-C_7)$-cycloalkyl, phenyl, pyrrolyl, imidazolyl, thiazolyl, azetidinyl, thienyl, piperidinyl, pyrrolidinyl, morpholinyl, pyridyl-methyl, or furyl, wherein cycloalkyl, phenyl, pyrrolyl, imidazolyl, thiazolyl, azetidinyl, thienylmethyl, piperidinyl, pyrrolidinyl, morpholinyl, pyridyl or furyl may in each case be optionally substituted up to twice by one or two of the following radicals:
    Cl, F, CN, $CF_3$, $OCF_3$, COOH, COO—$(C_1-C_6)$-alkyl, $CONH_2$, CONH—$(C_1-C_6)$-alkyl, CON—[$(C_1-C_6)$-alkyl]$_2$, $(C_1-C_6)$-alkyl, OH, or O—$(C_1-C_6)$-alkyl.

11. A process for preparing a compound of the formula (I)

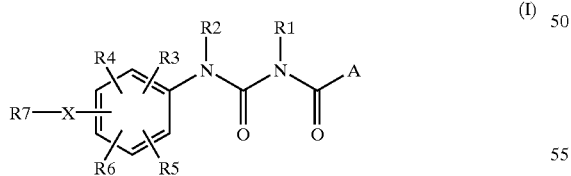

(I)

wherein

A is phenyl, or naphthyl,
  wherein the phenyl or naphthyl radical is optionally substituted up to three times by one or more of the following radicals:
    F, Cl, Br, OH, $CF_3$, $NO_2$, CN, $OCF_3$, O—$(C_1-C_6)$-alkyl, O—$(C_1-C_6)$-alkenyl, O—$(C_1-C_6)$-alkynyl, S—$(C_1-C_6)$-alkyl, S—$(C_1-C_6)$-alkenyl, S—$(C_1-C_6)$-alkynyl, SO—$(C_1-C_6)$-alkyl, $SO_2$—$(C_1-C_6)$-alkyl, $SO_2$—$NH_2$, $(C_1-C_6)$-alkyl, $(C_1-C_6)$-alkenyl, $(C_1-C_6)$-alkynyl, $(C_3-C_7)$-cycloalkyl, $(C_3-C_7)$-cycloalkyl-$(C_1-C_4)$-alkylene, $(C_0-C_6)$-alkylene-COOH, $(C_0-C_6)$-alkylene-COO$(C_1-C_7)$-alkyl, $CONH_2$, CONH$(C_1-C_6)$-alkyl, CON[$(C_1\_C_6)$-alkyl]$_2$, CONH$(C_3-C_6)$-cycloalkyl, (CO—$C_6)$-alkylene-$NH_2$, $(C_0-C_6)$-alkylene-NH$(C_2-C_6)$-alkyl, $(C_0-C_6)$-alkylene-N[$(C_1-C_6)$-alkyl]$_2$, NH—CO—$(C_1-C_6)$-Alkyl, NH—CO-phenyl, or NH—$SO_2$-phenyl, wherein the phenyl ring in NH—CO-phenyl, or NH—$SO_2$-phenyl is optionally substituted up to twice by one or two of the following radicals:
    F, Cl, CN, OH, $(C_1-C_6)$-alkyl, O—$(C_1-C_6)$-alkyl, $CF_3$, $OCF_3$, COOH, COO$(C_1-C_6)$-alkyl, or $CONH_2$;

R1, R2 are, independently of one another:
  H, $(C_1-C_6)$-alkyl, O—$(C_1-C_6)$-alkyl, CO—$(C_1-C_6)$-alkyl, COO—$(C_1-C_6)$-alkyl, $(C_1-C_6)$-alkylene-COOH, or $(C_1-C_6)$-alkylene-COO—$(C_1-C_6)$-alkyl;

R3, R4, R5, R6 are, independently of one another:
  H, F, Cl, Br, OH, $CF_3$, $NO_2$, CN, $OCF_3$, O—$(C_1-C_6)$-alkyl, O—$(C_1-C_6)$-alkenyl, O—$(C_1-C_6)$-alkynyl, S—$(C_1-C_6)$-alkyl, S—$(C_1-C_6)$-alkenyl, S—$(C_1-C_6)$-alkynyl, SO—$(C_1-C_6)$-alkyl, $SO_2$—$(C_1-C_6)$-alkyl, $SO_2$—$NH_2$, $(C_1-C_6)$-alkyl, $(C_1-C_6)$-alkenyl, $(C_1-C_6)$-alkynyl, $(C_3-C_7)$-cycloalkyl, $(C_3-C_7)$-cycloalkyl-$(C_{1-C4})$-alkylene, COOH, COO$(C_1-C_6)$-alkyl, $CONH_2$, CONH$(C_1-C_6)$-alkyl, CON[$(C_1-C_6)$-alkyl]$_2$, CONH$(C_3-C_7)$-cycloalkyl, $NH_2$, NH$(C_1-C_6)$-alkyl, N[$(C_1-C_6)$-alkyl]$_2$, NH—CO—$(C_1-C_6)$-alkyl, NH—CO-phenyl, or NH—$SO_2$-phenyl, wherein the phenyl ring in NH—CO-phenyl, or NH—$SO_2$-phenyl is optionally substituted up to twice by one or two of the following radicals:
    F, Cl, CN, OH, $(C_1-C_6)$-Alkyl, O—$(C_1-C_6)$-alkyl, $CF_3$, $OCF_3$, COOH, COO$(C_1-C_6)$-alkyl, or $CONH_2$;

X is O or S;

R7 is $(C_1-C_{10})$-alkylene-COOH, $(C_6-C_{10})$-alkylene-COO—$(C_1-C_6)$-alkyl, $(C_1-C_{10})$-alkylene-$CONH_2$, $(C_1-C_{10})$-alkylene-CONH—$(C_1-C_6)$-alkyl, $(C_1-C_{10})$-alkylene-CON—[$(C_1-C_6)$-alkyl]$_2$, $(C_1-C_{10})$-alkylene-$NH_2$, $(C_1-C_{10})$-alkylene-NH—$(C_1-C_6)$-alkyl, $(C_1-C_{10})$-alkylene-N[$(C_1-C_6)$-alkyl]$_2$, or $(C_1-C_{10})$-alkylene-B;
  wherein
  B is $(C_3-C_7)$-cycloalkyl, phenyl, pyrrolyl, imidazolyl, thiazolyl, azetidinyl, thienyl, piperidinyl, pyrrolidinyl, morpholinyl, pyridyl-methyl, or furyl, wherein cycloalkyl, phenyl, pyrrolyl, imidazolyl, thiazolyl, azetidinyl, thienylmethyl, piperidinyl, pyrrolidinyl, morpholinyl, pyridyl or furyl may in each case be optionally substituted up to twice by one or two of the following radicals:
    Cl, F, CN, $CF_3$, $OCF_3$, COOH, COO—$(C_1-C_6)$-alkyl, $CONH_2$, CONH—$(C_1-C_6)$-alkyl, CON—[$(C_1-C_6)$-alkyl]$_2$, $(C_1-C_6)$-alkyl, OH, or O—$(C_1-C_6)$-alkyl;

or a physiologically tolerated salt thereof,
except the compounds of the formula

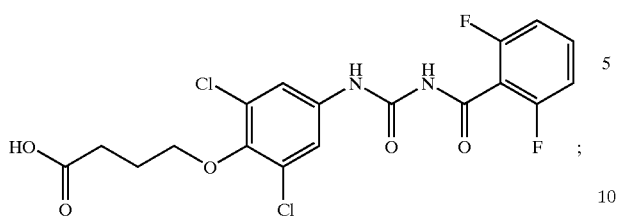

and

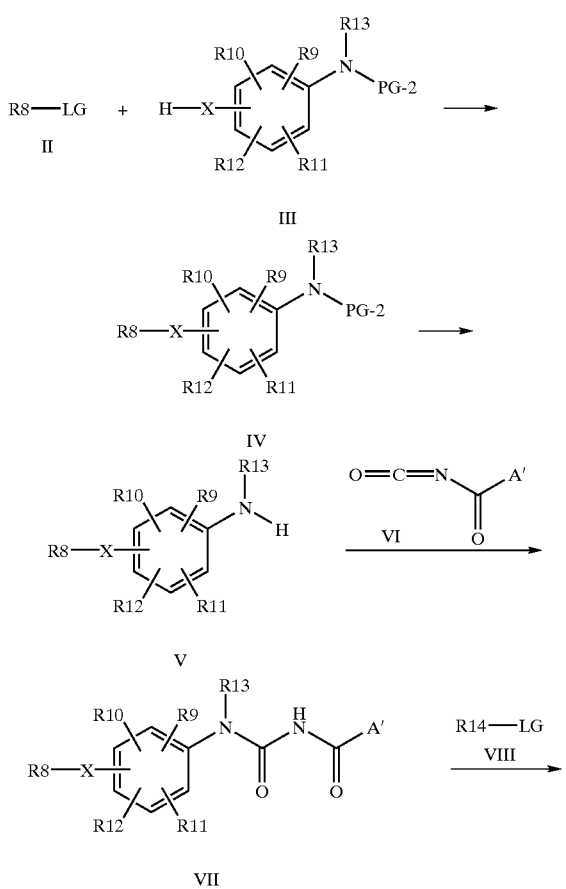

except compounds of the formula (I) in which the radicals are, at the same time:

| A | phenyl; |
|---|---|
| X | O; |
| R1 | H; |
| R7 | -($C_1$-$C_4$)-alkyl-B; |
| B | ($C_3$-$C_7$)-cycloalkyl, or heteroaryl; | according to the following diagram:

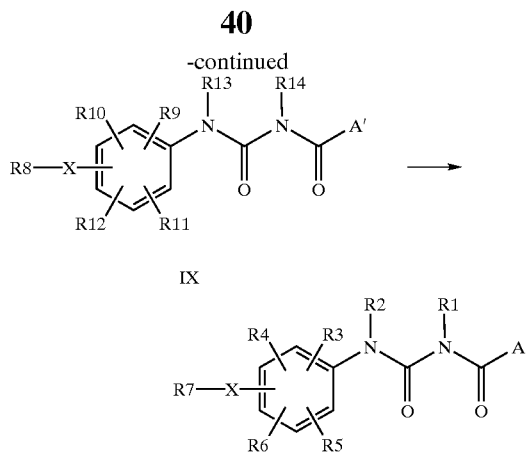

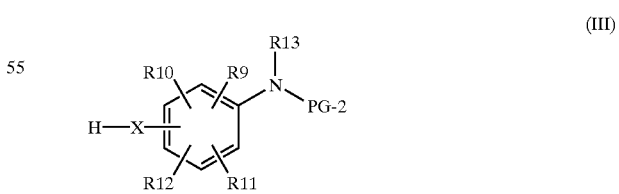

wherein the compounds of formula (II):

$$R8—LG \quad (II)$$

in which

R8 is ($C_1$-$C_{10}$)-alkylene-COO—(PG-1), ($C_6$-$C_{10}$)-alkylene-COO—($C_1$-$C_6$)-alkyl, ($C_1$-$C_{10}$)-alkylene-CON—(PG-2)$_2$, ($C_1$-$C_{10}$)-alkylene-CONH—($C_1$-$C_6$)-alkyl, ($C_1$-$C_{10}$)-alkylene-CON—[($C_1$-$C_6$)-alkyl]$_2$, ($C_1$-$C_{10}$)-alkylene-N—(PG-2)$_2$, $C_1$-$C_{10}$-alkylene-NH ($C_1$-$C_6$)-alkyl, ($C_1$-$C_{10}$)-alkylene-N[($C_1$-$C_6$)-alkyl]$_2$, or ($C_1$-$C_{10}$)-alkylene-B', PG-1 is a protective group for esters, PG-2 is a protective group for amino groups, which replaces either both hydrogens or only one hydrogen atom in the amino group, B' is ($C_3$-$C_7$)-cycloalkyl, ($C_3$-$C_7$)-cycloalkyl-($C_1$-$C_4$)-alkylene, phenyl, pyrrolyl, imidazolyl, thiazolyl, azetidinyl, thienyl, piperidinyl, pyrrolidinyl, morpholinyl, pyridyl and furyl wherein cycloalkyl, phenyl, pyrrolyl, imidazolyl, thiazolyl, azetidinyl, thienyl, piperidinyl, pyrrolidinyl, morpholinyl, pyridyl and furyl may, in each case, be optionally substituted up to twice by one or two of the following radicals:

Cl, F, CN, $CF_3$, $OCF_3$, COO—(PG-1), COO—($C_1$-$C_6$)-alkyl, CON—(PG-2)$_2$, CONH—($C_1$-$C_6$)-alkyl, CON—[($C_1$-$C_6$)-alkyl]$_2$, ($C_1$-$C_6$)-alkyl, O—(PG-3), O—($C_1$-$C_6$)-alkyl, PG-3 is a protective group for alcohols, and LG is a leaving group, is reacted with anilines of the formula (III):

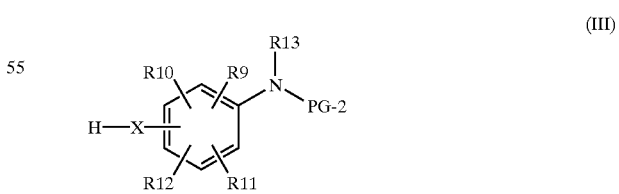

wherein X has the meaning as in claim 1 and PG-2 has the meaning described above, and wherein R9, R10, R11, R12 are, independently of one another: H, F, Cl, Br, O—(PG-3), $CF_3$, $NO_2$, CN, $OCF_3$, O—($C_1$-$C_6$)-alkyl, O—($C_1$-$C_6$)-alkenyl, O—$(C_1-C_6)$-alkynyl, S—$(C_1-C_6)$-alkyl, S—$(C_1-C_6)$-alkenyl, S—$(C_1-C_6)$-alkynyl, SO—$(C_1-C_6)$-alkyl, $SO_2$—$(C_1-C_6)$-alkyl, $SO_2$—N—(PG-2)$_2$, $(C_1-C_6)$-alkyl, $(C_1-C_6)$-alkenyl, $(C_1-C_6)$-alkynyl, $(C_3-C_7)$-cycloalkyl, $(C_3-C_7)$-cycloalkyl-$(C_1-C_4)$-alkylene, COO—(PG-1), COO$(C_1-C_6)$-alkyl, CON—(PG-2)$_2$, CONH$(C_1-C_6)$-alkyl, CON[$(C_1-C_6)$-alkyl]$_2$, CONH$(C_3-C_7)$-cycloalkyl, N—(PG-2)$_2$, NH$(C_1-C_6)$-alkyl, N[$(C_1-C_6)$-alkyl]$_2$, NH—CO—$(C_1-C_6)$-alkyl, NH—CO-phenyl, or NH—$SO_2$-phenyl, wherein the phenyl ring in NH—CO-phenyl, or NH—$SO_2$-phenyl, is optionally substituted up to twice by one or two of the following radicals:

F, Cl, CN, O—(PG-3), $(C_1-C_6)$-alkyl, O—$(C_1-C_6)$-alkyl, $CF_3$, $OCF_3$, COO—(PG-1), COO$(C_1-C_6)$-alkyl or CON—(PG-2)$_2$, R13 is H, $(C_1-C_6)$-alkyl, O—$(C_1-C_6)$-alkyl, CO—$(C_1-C_6)$-alkyl, COO—$(C_1-C_6)$-alkyl, $(C_1-C_6)$-alkylene-COO—(PG-1), or $(C_1-C_6)$-alkylene-COO—$(C_1-C_6)$-alkyl, and wherein PG-1, PG-2 and PG-3 have the meaning described above, to give compounds of the formula (IV):

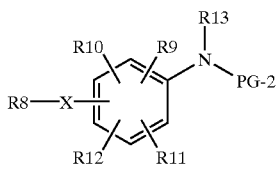
(IV)

wherein X, R8, R9, R10, R11, R12, R13 and PG-2 have the meaning described above;

selectively eliminating the protective group PG-2 to produce compounds of the formula (V):

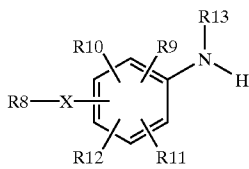
(V)

wherein X, R8, R9, R10, R11, R12, and R13 have the meanings stated above;

reacting compounds of the formula (V) with isocyanates of the formula (VI):

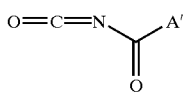
(VI)

wherein

A' is phenyl, or naphthyl, and wherein the phenyl or naphthyl radical is optionally substituted up to three times by F, Cl, Br, O—(PG-3), $CF_3$, $NO_2$, CN, $OCF_3$, O—$(C_1-C_6)$-alkyl, O—$(C_1-C_6)$-alkenyl, O—$(C_1-C_6)$-alkynyl, S—$(C_1-C_6)$-alkyl, S—$(C_1-C_6)$-alkenyl, S—$(C_1-C_6)$-alkynyl, SO—$(C_1-C_6)$-alkyl, $SO_2$—$(C_1-C_6)$-alkyl, $SO_2$—N—(PG-2)$_2$, $(C_1-C_6)$-alkyl, $(C_1-C_6)$-alkenyl, $(C_1-C_6)$-alkynyl, $(C_3-C_7)$-cycloalkyl, $(C_3-C_7)$-cycloalkyl-$(C_1-C_4)$-alkylene, $(C_0-C_6)$-alkylene-COO—(PG-1), $(C_0-C_6)$-alkylene-COO$(C_1-C_6)$-alkyl, CON—(PG-2)$_2$, CONH$(C_1-C_6)$-alkyl, CON[$(C_1-C_6)$-alkyl]$_2$, CONH$(C_3-C_7)$-cycloalkyl, (CO—$C_6$)-alkylene-N—(PG-2)$_2$, $(C_0-C_6)$-alkylene-NH$(C_1-C_6)$-alkyl, $(C_0-C_6)$-alkylene-N[$(C_1-C_6)$-alkyl]$_2$, NH—CO—$(C_1-C_6)$-alkyl, NH—CO-phenyl, or NH—$SO_2$-phenyl, wherein the phenyl ring in NH—CO-phenyl, or NH—$SO_2$-pheny is optionally substituted up to twice by one or two of the following radicals:

F, Cl, CN, O—(PG-3), $(C_1-C_6)$-alkyl, O—$(C_1-C_6)$-alkyl, $CF_3$, $OCF_3$, COO—(PG-1), COO$(C_1-C_6)$-alkyl or CON—(PG-2)$_2$, and PG-1, PG-2 and PG-3 have the meaning described above, to give compounds of the formula (VII):

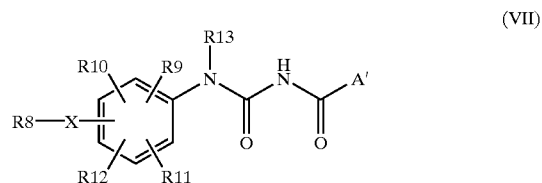
(VII)

wherein X, R8, R9, R10, R11, R12, R13 and A' have the meanings described above;

alkylating the compounds of the formula (VII), if R1 in compounds of the formula (I) is not a hydrogen atom, with compounds of the formula (VIII):

R14—LG  (VIII)

wherein

R14 is H, $(C_1-C_6)$-alkyl, O—$(C_1-C_6)$-alkyl, CO—$(C_1-C_6)$-alkyl, COO—$(C_1-C_6)$-alkyl, $(C_1-C_6)$-alkylene-COO—(PG-1), or $(C_1-C_6)$-alkylene-COO—$(C_1-C_6)$-alkyl, wherein LG and PG-1 have the meanings described above, to give compounds of formula (IX)

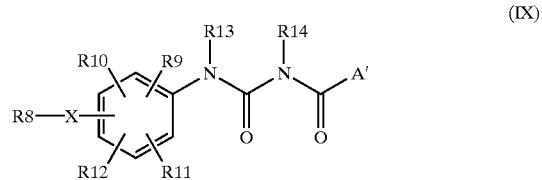
(IX)

wherein X, R8, R9, R10, R11, R12, R13, R14 and A' have the meanings described above, optionally eliminating the protective groups that are present in the radicals R8, R9, R10, R11, R12, R13, R14, A' and B' to give compounds of the formula (I), and optionally converting the compounds of the formula (I) into their salts.

12. The process according to claim 11, wherein PG-1 is $(C_1-C_6)$-alkyl, benzyl or p-methoxybenzyl.

13. The process according to claim 11, wherein PG-2 is $(C_1-C_6)$-alkylcarbonyl, $(C_1-C_6)$-alkyloxycarbonyl or $(C_6-C_{12})$-aryl-$(C_1-C_4)$-alkyloxycarbonyl.

14. The process according to claim 11, wherein PG-3 is benzyl, allyl, tetrahydropyranyl or tetrahydrofuranyl.

15. The process according to claim 11, wherein LG is halogen, arylsulfonyloxy or alkylsulfonyloxy.

16. The process according to claim 11, wherein the reaction of compounds of formula (II) with compounds of formula (III) is carried out in the presence of potassium or cesium carbonate.

17. The process according to claim 11, wherein the reaction of compounds of formula (II) with compounds of formula (III) is carried out in acetone or dimethylformamide.

18. The process according to claim 11, wherein the alkylation of compounds of formula (VII) with compounds of formula (VIII) is carried out in the presence of 1,8-diazabicyclo[5.4.0]undec-7-ene.

* * * * *

UNITED STATES PATENT AND TRADEMARK OFFICE
CERTIFICATE OF CORRECTION

PATENT NO.   : 6,506,778 B2
DATED          : January 14, 2003
INVENTOR(S) : Defossa et al.

It is certified that error appears in the above-identified patent and that said Letters Patent is hereby corrected as shown below:

Column 26,
Lines 54-55, "$(C_1-C_6)$-alkylene-COOH," should read -- $(C_0-C_6)$-alkylene-COOH, --.

Column 28,
Line 12, "$(C_1-C_6)$-alkylene," should read -- $(C_1-C_6)$-alkyl, --.

Column 30,
Line 25, "$(CO-C_6)$-alkylene-$NH_2$," should read -- $(C_0-C_6)$-alkylene-$NH_2$, --.
Lines 47-48, "CON[$(C_1-C_6)$-alkyl]2," should read -- CON[$(C_1-C_6)$-alkyl]$_2$, --.

Column 31,
Line 22, before "except compounds", insert -- and --.

Column 36,
Lines 57-58, "$(CO-C_6)$-alkylene-$NH_2$," should read -- $(C_0-C_6)$-alkylene-$NH_2$, --.

Column 37,
Line 16, "N[$(C_1-C_6)$-alkyl]2," should read -- N[$(C_1-C_6)$-alkyl]$_2$, --.

Column 38,
Line 6, "CON[$(C_{1.}C_6)$-alkyl]$_2$," should read -- CON[$(C_1-C_6)$-alkyl]$_2$, --.
Line 7, $(CO-C_6)$-alkylene-$NH_2$," should read -- $(C_0-C_6)$-alkylene-$NH_2$, --.
Line 31, "$(C_3-C_7)$-cycloalkyl-$(C_{1\text{-}C4})$-alkylene," should read -- $(C_3-C_7)$-cycloalkyl-$(C_1-C_4)$-alkylene, --.

Column 40,
Lines 29-30, "$C_1-C_{10}$)-alkylene-NH$(C_1-C_6)$-alkyl," should read -- $(C_1-C_{10})$-alkylene-NH$(C_1-C_6)$-alkyl, --.

UNITED STATES PATENT AND TRADEMARK OFFICE
CERTIFICATE OF CORRECTION

PATENT NO. : 6,506,778 B2
DATED : January 14, 2003
INVENTOR(S) : Defossa et al.

It is certified that error appears in the above-identified patent and that said Letters Patent is hereby corrected as shown below:

Column 42,
Lines 4-5, "(CO-$C_6$)-alkylene-N-(PG-2)$_2$," should read -- ($C_0$-$C_6$)-alkylene-N-(PG-2)$_2$, --.
Line 10, "NH-$SO_2$-pheny" should read -- NH-$SO_2$-phenyl --.
Line 41, after "formula (IX)", insert -- : --.

Signed and Sealed this

Twenty-ninth Day of July, 2003

JAMES E. ROGAN
*Director of the United States Patent and Trademark Office*